US011756674B2

(12) United States Patent
Fengler et al.

(10) Patent No.: US 11,756,674 B2
(45) Date of Patent: Sep. 12, 2023

(54) METHODS AND SYSTEMS FOR ADAPTIVE IMAGING FOR LOW LIGHT SIGNAL ENHANCEMENT IN MEDICAL VISUALIZATION

(71) Applicant: Stryker European Operations Limited, Carrigtwohill (IE)

(72) Inventors: John J. P. Fengler, North Vancouver (CA); Paul Roald Westwick, Vancouver (CA); Frederick Allen Moore, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 16/951,684

(22) Filed: Nov. 18, 2020

(65) Prior Publication Data
US 2021/0166806 A1 Jun. 3, 2021

Related U.S. Application Data

(63) Continuation of application No. 15/623,100, filed on Jun. 14, 2017, now Pat. No. 10,869,645.
(Continued)

(51) Int. Cl.
*G16H 30/40* (2018.01)
*G06T 5/50* (2006.01)
(Continued)

(52) U.S. Cl.
CPC ....... *G16H 30/40* (2018.01); *A61B 1/000095* (2022.02); *A61B 1/043* (2013.01);
(Continued)

(58) Field of Classification Search
CPC .... G16H 30/40; A61B 1/00009; A61B 1/043; A61B 1/045; A61B 1/05; A61B 1/0638;
(Continued)

(56) References Cited

U.S. PATENT DOCUMENTS

| 1,290,744 A | 1/1919 | Hollander |
| D62,892 S | 8/1923 | Dinkelspiel |

(Continued)

FOREIGN PATENT DOCUMENTS

| CN | 2076516 U | 5/1991 |
| CN | 101726980 A | 6/2010 |

(Continued)

OTHER PUBLICATIONS

US 6,692,429 B1, 02/2004, Imaizumi et al. (withdrawn)
(Continued)

*Primary Examiner* — Michael E Teitelbaum
(74) *Attorney, Agent, or Firm* — MORRISON & FOERSTER LLP

(57) ABSTRACT

Adaptive imaging methods and systems for generating enhanced low light video of an object for medical visualization are disclosed and include acquiring, with an image acquisition assembly, a sequence of reference frames and/or a sequence of low light video frames depicting the object, assessing relative movement between the image acquisition assembly and the object based on at least a portion of the acquired sequence of reference video frames or the acquired sequence of low light video frames, adjusting a level of image processing of the low light video frames based at least in part on the relative movement between the image acquisition assembly and the object, and generating a characteristic low light video output from a quantity of the low light video frames, wherein the quantity of the low light video frames is based on the adjusted level of image processing of the low light video frames.

24 Claims, 13 Drawing Sheets

Related U.S. Application Data

(60) Provisional application No. 62/350,121, filed on Jun. 14, 2016.

(51) Int. Cl.

| | |
|---|---|
| *A61B 5/00* | (2006.01) |
| *A61B 1/06* | (2006.01) |
| *A61B 1/05* | (2006.01) |
| *A61B 1/04* | (2006.01) |
| *A61B 1/07* | (2006.01) |
| *A61B 1/045* | (2006.01) |
| *A61B 1/00* | (2006.01) |
| *H04N 23/11* | (2023.01) |
| *H04N 23/70* | (2023.01) |
| *H04N 23/74* | (2023.01) |
| *H04N 23/951* | (2023.01) |
| *A61B 6/00* | (2006.01) |
| *G02B 23/12* | (2006.01) |
| *G06T 5/00* | (2006.01) |
| *A61B 5/11* | (2006.01) |
| *A61B 1/313* | (2006.01) |
| *H04N 23/50* | (2023.01) |

(52) U.S. Cl.
CPC .......... *A61B 1/045* (2013.01); *A61B 1/05* (2013.01); *A61B 1/0638* (2013.01); *A61B 1/0655* (2022.02); *A61B 1/0669* (2013.01); *A61B 1/0684* (2013.01); *A61B 1/07* (2013.01); *A61B 5/0071* (2013.01); *A61B 6/481* (2013.01); *A61B 6/5205* (2013.01); *G02B 23/12* (2013.01); *G06T 5/001* (2013.01); *G06T 5/50* (2013.01); *H04N 23/11* (2023.01); *H04N 23/70* (2023.01); *H04N 23/74* (2023.01); *H04N 23/951* (2023.01); *A61B 1/00186* (2013.01); *A61B 1/0646* (2013.01); *A61B 1/3132* (2013.01); *A61B 5/1121* (2013.01); *A61B 5/6869* (2013.01); *A61B 5/6875* (2013.01); *A61B 5/7221* (2013.01); *A61B 5/7264* (2013.01); *A61B 2505/05* (2013.01); *A61B 2562/0219* (2013.01); *A61B 2562/0233* (2013.01); *A61B 2576/00* (2013.01); *G06T 2207/10064* (2013.01); *G06T 2207/10068* (2013.01); *G06T 2207/20008* (2013.01); *G06T 2207/30004* (2013.01); *H04N 23/555* (2023.01)

(58) Field of Classification Search
CPC ....... A61B 1/0669; A61B 1/0684; A61B 1/07; A61B 5/0071; A61B 6/481; A61B 6/5205; A61B 1/00186; A61B 1/0646; A61B 1/3132; A61B 5/1121; A61B 5/6869; A61B 5/6875; A61B 5/7221; A61B 5/7264; A61B 2505/05; A61B 2562/0219; A61B 2562/0233; A61B 2576/00; A61B 1/000095; A61B 1/0655; G02B 23/12; G06T 5/001; G06T 5/50; G06T 2207/10064; G06T 2207/10068; G06T 2207/20008; G06T 2207/30004; H04N 5/23232; H04N 5/235; H04N 5/2354; H04N 5/332; H04N 2005/2255; H04N 23/11; H04N 23/70; H04N 23/74; H04N 23/951; H04N 23/555
See application file for complete search history.

(56) References Cited

U.S. PATENT DOCUMENTS

| | | |
|---|---|---|
| 2,453,336 A | 11/1948 | Orser |
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,158,504 A | 6/1979 | de Ponteves et al. |
| 4,200,801 A | 4/1980 | Schuresko |
| 4,260,217 A | 4/1981 | Traeger et al. |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,638,365 A | 1/1987 | Kato |
| 4,656,508 A | 4/1987 | Yokota |
| 4,660,982 A | 4/1987 | Okada |
| 4,688,905 A | 8/1987 | Okamura |
| 4,717,952 A | 1/1988 | Kohayakawa et al. |
| 4,742,388 A | 5/1988 | Cooper et al. |
| 4,768,513 A | 9/1988 | Suzuki |
| 4,786,813 A | 11/1988 | Svanberg et al. |
| 4,799,104 A | 1/1989 | Hosoya et al. |
| 4,806,005 A | 2/1989 | Schneider et al. |
| 4,821,117 A | 4/1989 | Sekiguchi |
| 4,837,625 A | 6/1989 | Douziech et al. |
| 4,852,985 A | 8/1989 | Fujihara et al. |
| 4,856,495 A | 8/1989 | Tohjoh et al. |
| 4,885,634 A | 12/1989 | Yabe |
| 4,895,145 A | 1/1990 | Joffe et al. |
| 4,930,516 A | 6/1990 | Alfano et al. |
| 4,930,883 A | 6/1990 | Salzman |
| 4,951,135 A | 8/1990 | Sasagawa et al. |
| 4,953,539 A | 9/1990 | Nakamura et al. |
| 4,954,897 A | 9/1990 | Ejima et al. |
| 4,974,936 A | 12/1990 | Ams et al. |
| 5,001,556 A | 3/1991 | Nakamura et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,134,662 A | 7/1992 | Bacus et al. |
| 5,159,398 A | 10/1992 | Maekewa et al. |
| 5,165,079 A | 11/1992 | Schulz-Hennig |
| 5,205,280 A | 4/1993 | Dennison, Jr. et al. |
| 5,208,651 A | 5/1993 | Buican |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,282,082 A | 1/1994 | Espie et al. |
| 5,295,017 A | 3/1994 | Brown |
| RE34,622 E | 5/1994 | Ledley |
| D346,921 S | 5/1994 | Stallsmith |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |

(56) References Cited

U.S. PATENT DOCUMENTS

| | | | |
|---|---|---|---|
| 5,408,263 | A | 4/1995 | Kikuchi et al. |
| 5,410,363 | A | 4/1995 | Capen et al. |
| 5,419,323 | A | 5/1995 | Kittrell et al. |
| 5,420,628 | A | 5/1995 | Poulsen et al. |
| 5,421,337 | A | 6/1995 | Richards-Kortum et al. |
| 5,424,841 | A | 6/1995 | Van Gelder et al. |
| 5,426,530 | A | 6/1995 | Copenhaver et al. |
| 5,430,476 | A | 7/1995 | Häfele et al. |
| D362,435 | S | 9/1995 | Charych et al. |
| 5,481,401 | A | 1/1996 | Kita et al. |
| 5,485,203 | A | 1/1996 | Nakamura et al. |
| 5,490,015 | A | 2/1996 | Umeyama et al. |
| 5,507,287 | A | 4/1996 | Palcic et al. |
| 5,515,449 | A | 5/1996 | Tsuruoka et al. |
| 5,535,052 | A | 7/1996 | Jörgens |
| 5,536,236 | A | 7/1996 | Yabe et al. |
| 5,557,451 | A | 9/1996 | Copenhaver et al. |
| 5,582,168 | A | 12/1996 | Samuels et al. |
| 5,585,846 | A | 12/1996 | Kim |
| 5,590,660 | A | 1/1997 | MacAulay et al. |
| 5,596,654 | A | 1/1997 | Tanaka |
| 5,646,680 | A | 7/1997 | Yajima |
| 5,647,368 | A | 7/1997 | Zeng et al. |
| 5,647,840 | A | 7/1997 | D'Amelio et al. |
| 5,667,472 | A | 9/1997 | Finn et al. |
| 5,677,724 | A | 10/1997 | Takizawa et al. |
| 5,682,567 | A | 10/1997 | Spruck et al. |
| 5,689,354 | A | 11/1997 | Orino |
| 5,695,049 | A | 12/1997 | Bauman |
| 5,697,373 | A | 12/1997 | Richards-Kortum et al. |
| 5,713,364 | A | 2/1998 | DeBaryshe et al. |
| 5,729,382 | A | 3/1998 | Morita et al. |
| 5,749,830 | A | 5/1998 | Kaneko et al. |
| 5,769,792 | A | 6/1998 | Palcic et al. |
| 5,772,355 | A | 6/1998 | Ross et al. |
| 5,772,580 | A | 6/1998 | Utsui et al. |
| 5,827,190 | A | 10/1998 | Palcic et al. |
| 5,833,617 | A | 11/1998 | Hayashi |
| 5,838,001 | A | 11/1998 | Minakuchi et al. |
| 5,840,017 | A | 11/1998 | Furuswaba et al. |
| 5,852,498 | A | 12/1998 | Youvan et al. |
| 5,891,016 | A | 4/1999 | Utsui et al. |
| 5,897,269 | A | 4/1999 | Ross et al. |
| 5,971,918 | A | 10/1999 | Zanger |
| 5,973,315 | A | 10/1999 | Saldana et al. |
| 5,984,861 | A | 11/1999 | Crowley |
| 5,986,271 | A | 11/1999 | Lazarev et al. |
| 5,986,642 | A | 11/1999 | Ueda et al. |
| 5,990,996 | A | 11/1999 | Sharp |
| 5,999,240 | A | 12/1999 | Sharp et al. |
| 6,002,137 | A | 12/1999 | Hayashi |
| 6,004,263 | A | 12/1999 | Nakaichi et al. |
| 6,008,889 | A | 12/1999 | Zeng et al. |
| 6,021,344 | A | 2/2000 | Lui et al. |
| 6,028,622 | A | 2/2000 | Suzuki |
| 6,030,339 | A | 2/2000 | Tatsuno et al. |
| 6,059,719 | A | 5/2000 | Yamamoto et al. |
| 6,059,720 | A | 5/2000 | Furusawa et al. |
| 6,061,591 | A | 5/2000 | Freitag et al. |
| 6,069,689 | A | 5/2000 | Zeng et al. |
| 6,070,096 | A | 5/2000 | Hayashi |
| 6,095,982 | A | 8/2000 | Richards-Kortum et al. |
| 6,099,466 | A | 8/2000 | Sano et al. |
| 6,110,106 | A | 8/2000 | MacKinnon et al. |
| 6,120,435 | A | 9/2000 | Eino |
| 6,147,705 | A | 11/2000 | Krauter et al. |
| 6,148,227 | A | 11/2000 | Wagnières et al. |
| 6,161,035 | A | 12/2000 | Furusawa |
| 6,181,414 | B1 | 1/2001 | Raz et al. |
| 6,192,267 | B1 | 2/2001 | Scherninski et al. |
| 6,212,425 | B1 | 4/2001 | Irion et al. |
| 6,226,126 | B1 | 5/2001 | Conemac |
| 6,258,576 | B1 | 7/2001 | Richards-Kortum et al. |
| D446,524 | S | 8/2001 | Bontly et al. |
| 6,280,378 | B1 | 8/2001 | Kazuhiro et al. |
| 6,293,911 | B1 | 9/2001 | Imaizumi et al. |
| 6,315,712 | B1 | 11/2001 | Rovegno |
| 6,332,092 | B1 | 12/2001 | Deckert et al. |
| 6,364,829 | B1 | 4/2002 | Fulghum |
| 6,364,831 | B1 | 4/2002 | Crowley |
| 6,377,842 | B1 | 4/2002 | Pogue et al. |
| D456,809 | S | 5/2002 | Schieffers |
| 6,419,628 | B1 | 7/2002 | Rudischhauser et al. |
| 6,422,994 | B1 | 7/2002 | Kaneko et al. |
| 6,462,770 | B1 | 10/2002 | Cline et al. |
| 6,510,338 | B1 | 1/2003 | Irion et al. |
| 6,526,213 | B1 | 2/2003 | Ilenda et al. |
| 6,529,239 | B1 | 3/2003 | Dyck et al. |
| 6,529,768 | B1 | 3/2003 | Hakamata |
| 6,537,211 | B1 | 3/2003 | Wang et al. |
| 6,544,102 | B2 | 4/2003 | Schäfer et al. |
| 6,571,119 | B2 | 5/2003 | Hayashi |
| 6,596,996 | B1 | 7/2003 | Stone et al. |
| 6,603,552 | B1 | 8/2003 | Cline et al. |
| 6,639,664 | B2 | 10/2003 | Haan et al. |
| 6,652,452 | B1 | 11/2003 | Seifert et al. |
| D483,668 | S | 12/2003 | Le Roux |
| 6,750,971 | B2 | 6/2004 | Overbeck et al. |
| 6,772,003 | B2 | 8/2004 | Kaneko et al. |
| 6,773,392 | B2 | 8/2004 | Kikuchi et al. |
| 6,786,865 | B2 | 9/2004 | Dhindsa |
| 6,821,245 | B2 | 11/2004 | Cline et al. |
| 6,826,424 | B1 | 11/2004 | Zeng et al. |
| 6,898,458 | B2 | 5/2005 | Zeng et al. |
| 6,899,675 | B2 | 5/2005 | Cline et al. |
| 6,922,583 | B1 | 7/2005 | Perelman et al. |
| 6,958,862 | B1 | 10/2005 | Joseph |
| 6,960,165 | B2 | 11/2005 | Ueno et al. |
| 7,043,291 | B2 | 5/2006 | Sendai |
| D524,985 | S | 7/2006 | Lukan et al. |
| D524,987 | S | 7/2006 | Lukan et al. |
| 7,150,552 | B2 | 12/2006 | Weidel |
| 7,179,222 | B2 | 2/2007 | Imaizumi et al. |
| 7,235,045 | B2 | 6/2007 | Wang et al. |
| 7,236,815 | B2 | 6/2007 | Richards-Kortum et al. |
| 7,253,894 | B2 | 8/2007 | Zeng et al. |
| 7,324,674 | B2 | 1/2008 | Ozawa et al. |
| 7,333,270 | B1 | 2/2008 | Pochapsky et al. |
| 7,341,557 | B2 | 3/2008 | Cline et al. |
| D567,649 | S | 4/2008 | Borkowski et al. |
| 7,385,772 | B2 | 6/2008 | Forkey et al. |
| 7,420,151 | B2 | 9/2008 | Fengler et al. |
| 7,479,990 | B2 | 1/2009 | Imaizumi et al. |
| D599,799 | S | 9/2009 | Di Bari et al. |
| D603,408 | S | 11/2009 | Fitch |
| D606,544 | S | 12/2009 | Di Bari et al. |
| 7,697,975 | B2 | 4/2010 | Zeng |
| 7,704,206 | B2 | 4/2010 | Suzuki et al. |
| 7,722,534 | B2 | 5/2010 | Cline et al. |
| 7,777,191 | B2 * | 8/2010 | Olcott ................ A61B 6/4258 250/362 |
| 7,798,955 | B2 | 9/2010 | Ishihara et al. |
| 7,811,229 | B2 | 10/2010 | Sugimoto |
| 7,928,352 | B2 | 4/2011 | Toda |
| D646,315 | S | 10/2011 | Orf |
| 8,035,067 | B2 | 10/2011 | Toda |
| D653,811 | S | 2/2012 | BenZion |
| 8,140,147 | B2 | 3/2012 | Maynard et al. |
| 8,285,015 | B2 | 10/2012 | Demos |
| 8,337,400 | B2 | 12/2012 | Mizuyoshi |
| 8,361,775 | B2 | 1/2013 | Flower |
| D677,258 | S | 3/2013 | Mistkawi |
| 8,408,269 | B2 | 4/2013 | Fengler et al. |
| 8,408,772 | B2 | 4/2013 | Li |
| D682,277 | S | 5/2013 | Tasselli et al. |
| 8,448,867 | B2 | 5/2013 | Liu et al. |
| 8,473,035 | B2 | 6/2013 | Frangioni |
| 8,498,695 | B2 | 7/2013 | Westwick et al. |
| D692,004 | S | 10/2013 | Man |
| D692,576 | S | 10/2013 | Steinman et al. |
| D692,892 | S | 11/2013 | Mistkawi |
| D693,802 | S | 11/2013 | Wikel |
| 8,630,698 | B2 | 1/2014 | Fengler et al. |
| 8,721,532 | B2 | 5/2014 | Takei et al. |

(56) References Cited

U.S. PATENT DOCUMENTS

| | | |
|---|---|---|
| 8,736,748 B2 | 5/2014 | Takita |
| 8,759,243 B2 | 6/2014 | Coffy et al. |
| 8,773,756 B2 | 7/2014 | Tesar et al. |
| 8,790,253 B2 | 7/2014 | Sunagawa et al. |
| 8,796,699 B2 | 8/2014 | So et al. |
| 8,830,339 B2 | 9/2014 | Velarde et al. |
| 8,849,380 B2 | 9/2014 | Patwardhan |
| D719,574 S | 12/2014 | Alegiani et al. |
| 8,961,403 B2 | 2/2015 | Cline et al. |
| D723,563 S | 3/2015 | Alegiani |
| 8,979,301 B2 | 3/2015 | Moore |
| D726,186 S | 4/2015 | Jenkins et al. |
| D734,339 S | 7/2015 | Zhou et al. |
| 9,125,552 B2 | 9/2015 | Dunki-Jacobs et al. |
| 9,143,746 B2 | 9/2015 | Westwick et al. |
| D742,509 S | 11/2015 | Anderson |
| 9,173,554 B2 | 11/2015 | Fengler et al. |
| D749,598 S | 2/2016 | Ray et al. |
| 9,282,305 B2 | 3/2016 | Kikuchi |
| 9,294,691 B2 | 3/2016 | Ooki |
| 9,295,392 B2 | 3/2016 | Douplik et al. |
| 9,357,931 B2 | 6/2016 | Nahm et al. |
| 9,386,909 B2 | 7/2016 | Fengler et al. |
| D764,565 S | 8/2016 | Tekunoff et al. |
| 9,407,838 B2 | 8/2016 | Butte et al. |
| 9,435,496 B2 | 9/2016 | Moore |
| 9,577,012 B2 | 2/2017 | Ooki |
| D782,901 S | 4/2017 | Richter |
| 9,642,532 B2 | 5/2017 | Fengler et al. |
| D791,137 S | 7/2017 | Wang et al. |
| 9,814,378 B2 | 11/2017 | Moore |
| D815,928 S | 4/2018 | Rummel et al. |
| D826,234 S | 8/2018 | Zhou et al. |
| D834,583 S | 11/2018 | Janzen et al. |
| 10,134,815 B2 | 11/2018 | So et al. |
| D835,284 S | 12/2018 | Barker et al. |
| D835,285 S | 12/2018 | Barker et al. |
| 10,356,334 B2 | 7/2019 | Moore et al. |
| 10,694,151 B2 | 6/2020 | Westwick et al. |
| 10,694,152 B2 | 6/2020 | Westwick et al. |
| 10,721,410 B2 | 7/2020 | Moore et al. |
| 10,779,734 B2 | 9/2020 | Fengler et al. |
| 10,980,420 B2 | 4/2021 | Fengler et al. |
| 10,992,848 B2 | 4/2021 | Murray et al. |
| 11,025,867 B2 | 6/2021 | Westwick et al. |
| 11,298,024 B2 | 4/2022 | Fengler et al. |
| 2001/0016679 A1 | 8/2001 | Futatsugi et al. |
| 2001/0028458 A1 | 10/2001 | Xiao |
| 2001/0049473 A1 | 12/2001 | Hayashi |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0035330 A1 | 3/2002 | Cline et al. |
| 2002/0076480 A1 | 6/2002 | Hsieh et al. |
| 2002/0138008 A1 | 9/2002 | Tsujita et al. |
| 2002/0143243 A1 | 10/2002 | Geordakoudi et al. |
| 2002/0148902 A1 | 10/2002 | Schlieffers |
| 2002/0155619 A1 | 10/2002 | Kurihara et al. |
| 2002/0156380 A1 | 10/2002 | Feld et al. |
| 2002/0161282 A1 | 10/2002 | Fulghum |
| 2002/0161283 A1 | 10/2002 | Sendai |
| 2002/0161284 A1 | 10/2002 | Tanaka |
| 2002/0168096 A1 | 11/2002 | Hakamata et al. |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2002/0196335 A1 | 12/2002 | Ozawa |
| 2003/0001951 A1 | 1/2003 | Tsujita et al. |
| 2003/0002036 A1 | 1/2003 | Haan et al. |
| 2003/0042493 A1 | 3/2003 | Kazakevich |
| 2003/0063398 A1 | 4/2003 | Abe et al. |
| 2003/0080193 A1 | 5/2003 | Ryan et al. |
| 2003/0117491 A1 | 6/2003 | Avni et al. |
| 2003/0135092 A1 | 7/2003 | Cline et al. |
| 2003/0153811 A1 | 8/2003 | Muckner |
| 2003/0158470 A1 | 8/2003 | Wolters et al. |
| 2003/0191368 A1 | 10/2003 | Wang et al. |
| 2003/0216626 A1 | 11/2003 | Tsujita et al. |
| 2003/0229270 A1 | 12/2003 | Suzuki et al. |
| 2004/0006276 A1 | 1/2004 | Demos et al. |
| 2004/0010183 A1 | 1/2004 | Dhindsa |
| 2004/0020990 A1 | 2/2004 | Haven et al. |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0133073 A1 | 7/2004 | Berci et al. |
| 2004/0134990 A1 | 7/2004 | Fitch et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0186351 A1 | 9/2004 | Imaizumi et al. |
| 2004/0218115 A1 | 11/2004 | Kawana et al. |
| 2004/0225222 A1 | 11/2004 | Zeng et al. |
| 2004/0245350 A1 | 12/2004 | Zeng |
| 2004/0263643 A1 | 12/2004 | Imaizumi et al. |
| 2005/0011954 A1 | 1/2005 | Hennick et al. |
| 2005/0027166 A1 | 2/2005 | Matsumoto et al. |
| 2005/0096505 A1 | 5/2005 | Imaizumi et al. |
| 2005/0140270 A1 | 6/2005 | Henson et al. |
| 2005/0143627 A1 | 6/2005 | Cline et al. |
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0203421 A1 | 9/2005 | Zeng et al. |
| 2005/0225656 A1 | 10/2005 | Ihama |
| 2005/0256373 A1 | 11/2005 | Bar-Or et al. |
| 2005/0273011 A1 | 12/2005 | Hattery et al. |
| 2005/0280783 A1 | 12/2005 | Yamasaki et al. |
| 2005/0288593 A1 | 12/2005 | Geordakoudi et al. |
| 2006/0002141 A1 | 1/2006 | Ouderkirk et al. |
| 2006/0004292 A1 | 1/2006 | Beylin |
| 2006/0017913 A1 | 1/2006 | Kawamata et al. |
| 2006/0089554 A1 | 4/2006 | Ishihara et al. |
| 2006/0094109 A1 | 5/2006 | Trainer |
| 2006/0108509 A1 | 5/2006 | Franigioni et al. |
| 2006/0146322 A1 | 7/2006 | Komachi et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0241496 A1 | 10/2006 | Fengler et al. |
| 2006/0247537 A1 | 11/2006 | Matsumoto |
| 2006/0250696 A1 | 11/2006 | McGuire |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0152161 A1 | 7/2007 | Olcott et al. |
| 2007/0177152 A1 | 8/2007 | Tearney et al. |
| 2007/0203413 A1 | 8/2007 | Frangioni |
| 2007/0213593 A1 | 9/2007 | Nakaoka |
| 2007/0229309 A1 | 10/2007 | Tomita et al. |
| 2007/0276236 A1* | 11/2007 | Jong .............. G01S 7/52039 600/437 |
| 2008/0019615 A1 | 1/2008 | Schnee et al. |
| 2008/0021274 A1 | 1/2008 | Bayer et al. |
| 2008/0024868 A1 | 1/2008 | Okamura |
| 2008/0027280 A1 | 1/2008 | Fengler et al. |
| 2008/0039697 A1 | 2/2008 | Morishita |
| 2008/0064925 A1 | 3/2008 | Gill et al. |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0217411 A1 | 9/2008 | Ledwith et al. |
| 2008/0246920 A1 | 10/2008 | Buczek et al. |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |

(56) References Cited

U.S. PATENT DOCUMENTS

| | | |
|---|---|---|
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0218405 A1 | 9/2009 | Joseph et al. |
| 2009/0236541 A1 | 9/2009 | Lommes et al. |
| 2009/0285762 A1 | 11/2009 | Flower |
| 2009/0290149 A1 | 11/2009 | Roth |
| 2010/0061604 A1 | 3/2010 | Nahm et al. |
| 2010/0065641 A1 | 3/2010 | Liu et al. |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0111361 A1 | 5/2010 | Tan et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0198010 A1 | 8/2010 | Cline et al. |
| 2010/0208487 A1 | 8/2010 | Li |
| 2010/0277817 A1 | 11/2010 | Durell |
| 2010/0308116 A1 | 12/2010 | Sani et al. |
| 2011/0019992 A1 | 1/2011 | Orf |
| 2011/0032350 A1 | 2/2011 | Kikuchi et al. |
| 2011/0071403 A1 | 3/2011 | Sevick-Muraca et al. |
| 2011/0073658 A1 | 3/2011 | Vassura et al. |
| 2011/0158914 A1 | 6/2011 | Yamada et al. |
| 2011/0235017 A1 | 9/2011 | Iwasaki |
| 2011/0244506 A1 | 10/2011 | Sutter et al. |
| 2011/0270092 A1 | 11/2011 | Kang et al. |
| 2011/0279679 A1 | 11/2011 | Samuel et al. |
| 2011/0290889 A1 | 12/2011 | Tamburini et al. |
| 2011/0306877 A1 | 12/2011 | Dvorsky et al. |
| 2011/0309275 A1 | 12/2011 | Azimi et al. |
| 2012/0006897 A1 | 1/2012 | Barkan et al. |
| 2012/0013773 A1 | 1/2012 | Yoshino et al. |
| 2012/0026325 A1 | 2/2012 | Bunker et al. |
| 2012/0044462 A1 | 2/2012 | Kaji |
| 2012/0150046 A1 | 6/2012 | Watson et al. |
| 2012/0256002 A1 | 10/2012 | O'Donnell et al. |
| 2012/0292530 A1 | 11/2012 | Ono et al. |
| 2012/0319645 A1 | 12/2012 | O'Donnell et al. |
| 2013/0008964 A1 | 1/2013 | Hawley et al. |
| 2013/0237762 A1 | 9/2013 | Fengler et al. |
| 2014/0071328 A1 | 3/2014 | Miesak |
| 2014/0078378 A1 | 3/2014 | Demers et al. |
| 2014/0139893 A1 | 5/2014 | Sugiyama et al. |
| 2014/0184769 A1 | 7/2014 | Ishihara et al. |
| 2014/0186351 A1 | 7/2014 | Britta et al. |
| 2014/0187967 A1 | 7/2014 | Wood et al. |
| 2014/0192258 A1 | 7/2014 | Yang et al. |
| 2014/0194687 A1 | 7/2014 | Fengler et al. |
| 2015/0018690 A1 | 1/2015 | Kang et al. |
| 2015/0083932 A1 | 3/2015 | Rizo et al. |
| 2015/0230698 A1 | 8/2015 | Cline et al. |
| 2015/0320296 A1 | 11/2015 | Morita |
| 2015/0341551 A1 | 11/2015 | Perrin et al. |
| 2015/0381909 A1 | 12/2015 | Butte et al. |
| 2016/0035104 A1* | 2/2016 | Bigioi ............... G06T 7/223 348/208.1 |
| 2016/0041098 A1 | 2/2016 | Hirawake et al. |
| 2016/0044253 A1 | 2/2016 | Dainty et al. |
| 2016/0100763 A1 | 4/2016 | Fengler et al. |
| 2016/0173802 A1 | 6/2016 | Matsuo et al. |
| 2017/0196527 A1 | 7/2017 | Kokubun |
| 2017/0245803 A1 | 8/2017 | Ahmed et al. |
| 2018/0234603 A1 | 8/2018 | Moore et al. |
| 2021/0105393 A1 | 4/2021 | Moore et al. |
| 2021/0274131 A1 | 9/2021 | Westwick et al. |
| 2021/0307613 A1 | 10/2021 | Fengler et al. |
| 2022/0030149 A1 | 1/2022 | Moore et al. |

FOREIGN PATENT DOCUMENTS

| | | |
|---|---|---|
| CN | 101828139 A | 9/2010 |
| CN | 102026668 A | 4/2011 |
| CN | 201974160 U | 9/2011 |
| CN | 102257510 A | 11/2011 |
| CN | 103543609 A | 1/2014 |
| DE | 19535114 A1 | 3/1996 |
| DE | 19608027 A1 | 9/1996 |
| DE | 10028233 A1 | 1/2002 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 0671706 B1 | 6/1999 |
| EP | 1374755 A1 | 1/2004 |
| EP | 1 496 690 A2 | 1/2005 |
| EP | 1883337 A1 | 2/2008 |
| EP | 2051603 A1 | 4/2009 |
| EP | 2859837 A1 | 4/2015 |
| EP | 2 988 654 B1 | 6/2020 |
| FR | 2671405 A1 | 7/1992 |
| JP | S60-246733 A | 12/1985 |
| JP | S61-159936 A | 7/1986 |
| JP | H-01-135349 A | 5/1989 |
| JP | 03-97439 A | 4/1991 |
| JP | 03-97441 A | 4/1991 |
| JP | 03-97442 A | 4/1991 |
| JP | 05-115435 A | 5/1993 |
| JP | 06-125911 A | 5/1994 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | H07-204156 A | 8/1995 |
| JP | H07-222712 A | 8/1995 |
| JP | H07-250804 A | 10/1995 |
| JP | H07-250812 A | 10/1995 |
| JP | H07-327913 A | 12/1995 |
| JP | H08-126605 A | 5/1996 |
| JP | 08-140928 A2 | 6/1996 |
| JP | 08-140929 A2 | 6/1996 |
| JP | H08-224208 A | 9/1996 |
| JP | H08-224209 A | 9/1996 |
| JP | H08-224210 A | 9/1996 |
| JP | H08-224240 A | 9/1996 |
| JP | H08-252218 A | 10/1996 |
| JP | H09-19408 A | 1/1997 |
| JP | 09-066023 A2 | 3/1997 |
| JP | 09-070384 A2 | 3/1997 |
| JP | H10-127563 A | 5/1998 |
| JP | H10-151104 A | 6/1998 |
| JP | 10-225427 A2 | 8/1998 |
| JP | H10-201700 A | 8/1998 |
| JP | H10-201707 A | 8/1998 |
| JP | H10-225426 A | 8/1998 |
| JP | H10-243915 A | 9/1998 |
| JP | H10-243920 A | 9/1998 |
| JP | H10-308114 A | 11/1998 |
| JP | H10-309281 A | 11/1998 |
| JP | H10-309282 A | 11/1998 |
| JP | H10-321005 A | 12/1998 |
| JP | H10-328129 A | 12/1998 |
| JP | H11-47079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-113839 A | 4/1999 |
| JP | H11-155812 A | 6/1999 |
| JP | H11-244220 A | 9/1999 |
| JP | H11-332819 A | 12/1999 |
| JP | 2000-504968 A | 4/2000 |

(56) References Cited

FOREIGN PATENT DOCUMENTS

| | | | |
|---|---|---|---|
| JP | 2000-230903 A | 8/2000 |
| JP | 2000-245693 A | 9/2000 |
| JP | 2000-354583 A | 12/2000 |
| JP | 2001-78205 A | 3/2001 |
| JP | 2001-518241 A | 10/2001 |
| JP | 2002-000560 A | 1/2002 |
| JP | 02-049302 A | 2/2002 |
| JP | 2002-244122 A | 8/2002 |
| JP | 2003-045210 A | 2/2003 |
| JP | 2004-024611 A | 1/2004 |
| JP | 2004-094043 A | 3/2004 |
| JP | 2004-163902 A | 6/2004 |
| JP | 2004-520105 A | 7/2004 |
| JP | 2004-247156 A | 9/2004 |
| JP | 2004-289545 A | 10/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-149996 A | 6/2005 |
| JP | 2005-292404 A | 10/2005 |
| JP | 2005-326777 A | 11/2005 |
| JP | 2006-3103 A | 1/2006 |
| JP | 2006-073767 A | 3/2006 |
| JP | 2006-087764 A | 4/2006 |
| JP | 2006-525494 A | 11/2006 |
| JP | 2006-326153 A | 12/2006 |
| JP | 2007-029453 A | 2/2007 |
| JP | 2007-072392 A | 3/2007 |
| JP | 2007-089840 A | 4/2007 |
| JP | 2009-259703 A | 11/2009 |
| JP | 2010-107751 A | 5/2010 |
| JP | 2010-117442 A | 5/2010 |
| JP | 2010-524194 A | 7/2010 |
| JP | 2011-500921 A | 1/2011 |
| JP | 2011-072424 A | 4/2011 |
| JP | 2011-110272 A | 6/2011 |
| JP | 2011-169819 A | 9/2011 |
| JP | 2011-528918 A | 12/2011 |
| JP | 5231625 B2 | 7/2013 |
| JP | 2014-123941 A | 7/2014 |
| JP | 2015-16332 A | 1/2015 |
| JP | 5859578 B2 | 2/2016 |
| RU | 99592 U1 | 11/2010 |
| WO | WO-1993/04648 A1 | 3/1993 |
| WO | WO-1994/13191 A1 | 6/1994 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/42910 A1 | 7/2000 |
| WO | WO-2000/54652 A1 | 9/2000 |
| WO | WO-2002/007587 A2 | 1/2002 |
| WO | WO-2002/50518 A2 | 6/2002 |
| WO | WO-2003/059159 A2 | 7/2003 |
| WO | WO-2003/059159 A8 | 7/2003 |
| WO | WO-2006/116847 A1 | 11/2006 |
| WO | WO-2007/081707 A2 | 7/2007 |
| WO | WO-2008/011722 A1 | 1/2008 |
| WO | WO-2008/071240 A1 | 6/2008 |
| WO | WO-2009/033021 A2 | 3/2009 |
| WO | WO-2013/160279 A1 | 10/2013 |
| WO | WO-2014/176375 A2 | 10/2014 |
| WO | WO-2015/164774 A1 | 10/2015 |
| WO | WO-2016/055837 A1 | 4/2016 |

OTHER PUBLICATIONS

Alfano, R.R et al. (Oct. 1987). "Fluorescence Spectra From Cancerous and Normal Human Breast and Lung Tissues," *IEEE Journal of Quantum Electronics* QE-23(10):1806-1811.

Andersson-Engels, S. et al. (Mar. 1989). "Tissue Diagnostics Using Laser Induced Fluorescence," *Ber. Bunsenges Physical Chemistry* 93(3):335-342.

Australian Office Action dated Jun. 28, 2018 for Australian Patent Application No. 2016351730 filed on Nov. 10, 2016, five pages.

Australian Office Action dated May 10, 2019 for Australian Patent Application No. 2016351730 filed on Nov. 10, 2016, ten pages.

Bhunchet, E. et al. (Apr. 2002). "Fluorescein Electronic Endoscopy: a Novel Method for Detection of Early Stage Gastric Cancer Not Evident to Routine Endoscopy," *Gastrointestinal Endoscopy* 55(4):562-571.

Canadian Office Action dated Feb. 1, 2017 for Canadian Patent Application No. 171282, filed on Oct. 27, 2016, two pages.

Canadian Office Action dated Feb. 19, 2019 for CA Patent Application No. 2,998,920 filed on Mar. 16, 2018, four pages.

Chinese Notice of Allowance dated Jun. 19, 2017 for Chinese Patent Application No. 201280022284.3, filed on Nov. 7, 2013, four pages.

Chinese Office Action dated Jul. 29, 2016 for Chinese Patent Application No. 2012800222843 filed on Mar. 8, 2012, eight pages.

Chinese Office Action dated Mar. 14, 2017 for Chinese Patent Application No. 201280022284.3, filed on Nov. 7, 2013, seven pages.

Chinese Office Action dated Nov. 24, 2015 for Chinese Patent Application No. 2012800222843 filed on Mar. 8, 2012, sixteen pages.

Chinese Office Action dated Sep. 26, 2018 for Chinese Patent Application No. 2018092001857100, filed on Sep. 4, 2017, nineteen pages.

Dawson, J.B. et al. (Jul. 1980). "A Theoretical and Experimental Study of Light Absorption and Scattering by In Vivo Skin," *Phys. Med. Biol.* 25(4):695-709.

European Notice of Allowance dated Feb. 28, 2018 for EP Patent Application No. 12754208.2 filed Oct. 4, 2013, six pages.

European Notice of Allowance dated Jul. 12, 2018 for EP Patent Application No. 12754208.2 filed Oct. 4, 2013, two pages.

European Notice of Allowance dated Jun. 22, 2017 for EP Patent Application No. 08706262.6 filed on Aug. 21, 2009, two pages.

European Notice of Allowance dated Mar. 6, 2018 for EP Patent Application No. 13180297.7 filed Aug. 13, 2013, seven pages.

European Notice of Allowance dated Mar. 18, 2019 for EP Patent Application No. 09819758.5, filed on May 4, 2011, seven pages.

European Notice of Allowance dated May 25, 2018 for EP Patent Application No. 13180297.7 filed Aug. 13, 2013, two pages.

European Notice of Allowance dated Nov. 25, 2016 for EP Patent Application No. 08706262.6 filed on Aug. 21, 2009, eight pages.

European Office Action dated Apr. 6, 2017, for EP Patent Application No. 09819758.5, filed on May 4, 2011, five pages.

European Office Action dated Apr. 13, 2017, for EP Patent Application No. 12754208.2 filed on Oct. 4, 2013, five pages.

European Office Action dated Dec. 3, 2015 for EP Patent Application No. 08706262.6 filed on Jan. 23, 2008; fifteen pages.

European Office Action dated Jan. 23, 2017 for EP Patent Application No. 16186321.2 filed on Aug. 30, 2016, two pages.

European Office Action dated Nov. 3, 2015 for EP Patent Application No. 12754208.2 filed Oct. 4, 2013, four pages.

European Office Action dated Nov. 19, 2015 for EP Patent Application No. 07 785 001.4, filed on Jul. 30, 2007, four pages.

European Office Action dated Sep. 29, 2015, for EP Patent Application No. 09721252.6 filed Mar. 18, 2009; five pages.

European Search Report dated Dec. 21, 2016 for EP Patent Application No. 16186321.2 filed on Aug. 30, 2016, nine pages.

European Search Report dated Jan. 24, 2012 for EP Patent Application No. 07785001.4 filed on Jul. 30, 2007, seven pages.

European Search Report dated Jul. 17, 2014 for EP Patent Application No. 09721252.6 filed Mar. 18, 2009; eleven pages.

European Search Report dated Oct. 1, 2014 for EP Patent Application No. 12754208.2 filed on Mar. 8, 2012, five pages.

European Search Report dated Oct. 9, 2013, for European Patent Application No. 06721854.5, filed on May 4, 2005, seven pages.

European Search Report dated Sep. 20, 2013 for EP Patent Application No. 08706262.6 filed on Jan. 23, 2008, five pages.

(56) References Cited

OTHER PUBLICATIONS

Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.
Georgakoudi, I et al. (Apr. 2005). "Characterization of Dysplastic Tissue Morphology and Biochemistry in Barrett's Esophagus using Diffuse Reflectance and Light Scattering Spectroscopy," *Techniques in Gastrointestinal Endoscopy* 7(2):100-105.
Hubel, P.M. et al. (2004). "Spatial Frequency Response of Color Image Sensors: Bayer Color Filters and Foveon X3," *Proceedings of SPIE* 5301:402-406.
Hung, J. et al. (1991). "Autofluorescence of Normal and Malignant Bronchial Tissue," *Lasers in Surgery and Medicine* 11(2):99-105.
Indian Office Action dated Jan. 31, 2018 for Indian Patent Application No. 6532/DELNP/2010 filed on Sep. 16, 2010, five pages.
Indian Office Action dated Jun. 26, 2018 for Indian Patent Application No. 8678/DELNP/2013 filed on Mar. 8, 2012, five pages.
International Preliminary Report on Patentability dated Dec. 27, 2018 for International Patent Application No. PCT/CA2017/050734 filed on Jun. 14, 2017, six pages.
International Preliminary Report on Patentability dated Feb. 3, 2009 for International Patent Application No. PCT/CA2007/001335 filed on Jul. 30, 2007, five pages.
International Preliminary Report on Patentability dated May 24, 2018 for International Patent Application No. PCT/CA2016/051315 filed on Nov. 10, 2016, nine pages.
International Preliminary Report on Patentability dated Nov. 6, 2007 for International Patent Application No. PCT/CA2006/000669, filed on Apr. 27, 2006, nine pages.
International Preliminary Report on Patentability dated Sep. 21, 2010 for International Patent Application No. PCT/US2009/037506, filed on Mar. 18, 2009, seven pages.
International Search Report and written Opinion dated Apr. 24, 2017 for International Patent Application No. PCT/CA2017/050083, filed on Jan. 26, 2017, seven pages.
International Search Report and written Opinion dated Feb. 10, 2017 for International Patent Application No. PCT/CA2016/051315 filed on Nov. 10, 2016, thirteen pages.
International Search Report and Written Opinion dated Sep. 18, 2017 for International Patent Application No. PCT/CA2017/050734, filed on Jun. 14, 2017, eight pages.
International Search Report dated Aug. 3, 2006, for International Patent Application No. PCT/CA2006/000669, filed on Apr. 27, 2006, three pages.
International Search Report dated Aug. 3, 2012, for International Patent Application No. PCT/IB2012/000601, filed on Mar. 8, 2012, three pages.
International Search Report dated Dec. 7, 2007, for International Patent Application No. PCT/CA2007/001335, filed on Jul. 30, 2007, two pages.
International Search Report dated Jan. 21, 2002 for International Patent Application No. PCT/US2001/022198, filed on Jul. 13, 2001, three pages.
International Search Report dated Jul. 22, 2009 for International Patent Application No. PCT/US09/37506, filed on Mar. 18, 2009, two pages.
International Search Report dated May 13, 2008 for Intentional Patent Application No. PCT/CA2008/00015, filed on Jan. 8, 2008, one page.
Invitation to Pay additional Fees and, where Applicable, Protest Fee, dated Dec. 22, 2016 for International Patent Application No. PCT/CA2016/051315, filed on Nov. 10, 2016, two pages.
Japanese Final Office Action dated Aug. 2, 2013 for Japanese Application No. 2008-509275, filed on Apr. 27, 2006, four pages.
Japanese Notice of Allowance dated Apr. 2, 2018 for Japanese Patent Application No. 2017-018858 filed on Feb. 3, 2017, six pages.
Japanese Notice of Allowance dated Jan. 5, 2017 for Japanese Patent Application No. 2015-238784, filed on Dec. 7, 2015, six pages.
Japanese Notice of Allowance dated Nov. 17, 2017 for Japanese Application No. 2016-253736 filed on Dec. 27, 2016, six pages.
Japanese Notice of Allowance dated Nov. 28, 2016 for Japanese Patent Application No. 2015-245598, filed on Mar. 8, 2012, six pages.
Japanese Office Action dated Apr. 3, 2015 for Japanese Patent Application No. 2013-058356, filed Mar. 18, 2009, four pages.
Japanese Office Action dated Apr. 20, 2012 for Japanese Patent Application No. 2011-500921, filed Mar. 18, 2009, four pages.
Japanese Office Action dated Dec. 8, 2017 for Japanese Patent Application No. 2017-018858 filed on Feb. 3, 2017, six pages.
Japanese Office dated Dec. 26, 2012 for Japanese Patent Application No. 2011-500921, filed on Mar. 18, 2009, two pages.
Japanese Office Action dated Feb. 17, 2012 for Japanese Application No. 2008-509275, filed on Apr. 27, 2006, six pages.
Japanese Office Action dated Jul. 22, 2014 for Japanese Patent Application No. 2013-557187 filed Mar. 8, 2012, seven pages.
Japanese Office Action dated Mar. 9, 2015 for Japanese Patent Application No. 2013-557187, filed Mar. 8, 2012, five pages.
Japanese Office Action dated May 26, 2014 in Japanese Patent Application No. 2013-058356, filed on Mar. 18, 2009, w/Concise Explanation of the Relevance, three pages.
Japanese Office Action dated Nov. 11, 2011 for Japanese Application No. 2009-521077, filed on Jul. 30, 2007, four pages.
Japanese Office Action dated Sep. 14, 2012 for Japanese Application No. 2008-509275, filed on Apr. 27, 2006, seven pages.
Japanese Office Action dated Sep. 19, 2014 for Japanese Application No. 2013-246636, filed on Apr. 27, 2006, six pages.
Korean Decision on the Trial Against Final Rejection from the Intellectual Property Tribunal (IPT) dated Sep. 25, 2017 for Korean Patent Application No. 2013-7026479, filed on Oct. 7, 2013, seventeen pages.
Korean Notice of Allowance dated Dec. 13, 2017 for Korean Patent Application No. 10-2017-7008654, filed on Mar. 29, 2017, three pages.
Korean Notice of Allowance dated Jan. 2, 2017 for Korean Patent Application No. 10-2015-7033310, filed on Nov. 20, 2015, three pages.
Korean Office Action dated Aug. 20, 2015 for Korean Patent Application No. 20137026479 filed on Mar. 8, 2012, three pages.
Korean Office Action dated Aug. 30, 2016 for Korean Patent Application No. IQ-2015-7033310 filed on Mar. 8, 2012, seven pages.
Korean Office Action dated Dec. 8, 2015 for Korean Patent Application No. 20157033310 filed on Mar. 8, 2012, seven pages.
Korean Office Action dated Jun. 27, 2017 for Korean Patent Application No. 2017-7008654, filed on Mar. 29, 2017, ten pages.
Lyon, R.E. et al. (2002). "Eyeing the Camera: Into the Next Century," *10 Color and Imaging Conference Final Program & Proceedings* 349-355.
Russian Notice of Allowance dated Aug. 19, 2016 for Russian Patent Application No. 2013144845/07, filed on Mar. 8, 2012, thirteen pages.
Török, B. et al. (May 1996). "Simultane digitale Indocyaningrün- und Fluoreszeinangiographie (Simultaneous Digital ICG and Fluorescein Angiography)," *Klin Monatsbl Augenheilkd* 208(5):333-336, (with English Translation of the Introduction).
U.S. Final Office Action dated Apr. 24, 2015 for U.S. Appl. No. 12/933,512, filed Nov. 24, 2010, nineteen pages.
U.S. Final Office Action dated Aug. 7, 2017 for U.S. Appl. No. 15/343,038, filed Nov. 3, 2016, eleven pages.
U.S. Final Office Action dated Aug. 10, 2017 for U.S. Appl. No. 15/343,034, filed Nov. 3, 2016, twelve pages.
U.S. Final Office Action dated Aug. 11, 2017 for U.S. Appl. No. 14/860,687, filed Sep. 21, 2015, seventeen pages.
U.S. Final Office Action dated Dec. 14, 2018 for U.S. Appl. No. 15/584,405, filed May 2, 2017, seven pages.
U.S. Final Office Action dated Feb. 1, 2018 for U.S. Appl. No. 15/584,405, filed May 2, 2017, ten pages.

(56) References Cited

OTHER PUBLICATIONS

U.S. Final Office Action dated Feb. 27, 2017 for U.S. Appl. No. 15/247,419, filed Aug. 25, 2016, ten pages.
U.S. Final Office Action dated Jan. 11, 2019 for U.S. Appl. No. 15/343,038, filed Nov. 3, 2016, twelve pages.
U.S. Final Office Action dated Jan. 14, 2019 for U.S. Appl. No. 14/860,687, filed Sep. 21, 2015, sixteen pages.
U.S. Final Office Action dated Jan. 22, 2019 for U.S. Appl. No. 15/343,034, filed Nov. 3, 2016, twelve pages.
U.S. Final Office Action dated Jul. 23, 2008 for U.S. Appl. No. 11/122,267, filed May 4, 2016, six pages.
U.S. Final Office Action dated Jun. 5, 2014 for U.S. Appl. No. 12/761,462, filed Apr. 16, 2010, fourteen pages.
U.S. Final Office Action dated Jun. 18, 2015 for U.S. Appl. No. 14/154,177, filed Jan. 13, 2014, eight pages.
U.S. Final Office Action dated Mar. 22, 2016 for U.S. Appl. No. 14/873,842, filed Oct. 2, 2015, eighteen pages.
U.S. Final Office Action dated May 11, 2011 for U.S. Appl. No. 11/412,715, filed Apr. 26, 2006, eight pages.
U.S. Final Office Action dated May 21, 2012 for U.S. Appl. No. 11/964,330, filed Dec. 26, 2007, twelve pages.
U.S. Final Office Action dated Nov. 24, 2009 for U.S. Appl. No. 11/009,965, filed Dec. 10, 2004, fourteen pages.
U.S. Non Final Office Action dated Apr. 2, 2009 for U.S. Appl. No. 11/009,965, filed Dec. 10, 2004, thirteen pages.
U.S. Non Final Office Action dated Apr. 3, 2019 for U.S. Appl. No. 15/416,876, filed Jan. 26, 2017, thirteen pages.
U.S. Non Final Office Action dated Aug. 15, 2018 for U.S. Appl. No. 15/348,664, filed Nov. 10, 2016, eleven pages.
U.S. Non Final Office Action dated Aug. 16, 2013 for U.S. Appl. No. 12/761,462, filed Apr. 16, 2010, ten pages.
U.S. Non Final Office Action dated Aug. 16, 2013 for U.S. Appl. No. 12/761,523, filed Apr. 16, 2010, nine pages.
U.S. Non Final Office Action dated Dec. 10, 2010 for U.S. Appl. No. 11/412,715, filed Apr. 26, 2006, ten pages.
U.S. Non Final Office Action dated Dec. 14, 2011 for U.S. Appl. No. 11/412,715, filed Apr. 26, 2006, eight pages.
U.S. Non Final Office Action dated Feb. 1, 2017 for U.S. Appl. No. 14/860,687, filed Sep. 21, 2015, fifteen pages.
U.S. Non Final Office Action dated Feb. 3, 2010 for U.S. Appl. No. 11/626,308, filed Jan. 23, 2007, eleven pages.
U.S. Non Final Office Action dated Jan. 2, 2008 for U.S. Appl. No. 11/122,267, filed May 4, 2005, five pages.
U.S. Non Final Office Action dated Jan. 20, 2016 for U.S. Appl. No. 14/629,473, filed Feb. 23, 2015, fifteen pages.
U.S. Non Final Office Action dated Jan. 26, 2017 for U.S. Appl. No. 15/343,034, filed Nov. 3, 2016, seventeen pages.
U.S. Non Final Office Action dated Jan. 27, 2017 for U.S. Appl. No. 15/343,038, filed Nov. 3, 2016, fifteen pages.
U.S. Non Final Office Action dated Jul. 2, 2013 for U.S. Appl. No. 12/933,512, filed Nov. 24, 2010, twelve pages.
U.S. Non Final Office Action dated Jul. 17, 2003 for U.S. Appl. No. 09/905,642, filed Jul. 13, 2001, six pages.
U.S. Non Final Office Action dated Jun. 1, 2007 for U.S. Appl. No. 10/899,648, filed Jul. 26, 2004, seven pages.
U.S. Non Final Office Action dated Jun. 5, 2018 for U.S. Appl. No. 14/860,687, filed Sep. 21, 2015, eighteen pages.
U.S. Non Final Office Action dated Jun. 8, 2018 for U.S. Appl. No. 15/343,034, filed Nov. 3, 2016, thirteen pages.
U.S. Non Final Office Action dated Jun. 8, 2018 for U.S. Appl. No. 15/584,405, filed May 2, 2017, eight pages.
U.S. Non Final Office Action dated Jun. 9, 2011 for U.S. Appl. No. 11/830,323, filed Jul. 30, 2007, five pages.
U.S. Non Final Office Action dated Jun. 20, 2008 for U.S. Appl. No. 11/009,398, filed Dec. 10, 2004, fifteen pages.
U.S. Non Final Office Action dated Jun. 23, 2010 for U.S. Appl. No. 11/009,965, filed Dec. 10, 2004, fifteen pages.
U.S. Non Final Office Action dated Jun. 27, 2014 for U.S. Appl. No. 13/415,561, filed Mar. 3, 2012, fourteen pages.
U.S. Non Final Office Action dated May 18, 2004 for U.S. Appl. No. 10/050,601, filed Jan. 15, 2002, eight pages.
U.S. Non Final Office Action dated May 25, 2018 for U.S. Appl. No. 15/343,038, filed Nov. 3, 2016, eleven pages.
U.S. Non Final Office Action dated Nov. 5, 2014 for U.S. Appl. No. 13/930,225, filed Jun. 28, 2013, six pages.
U.S. Non Final Office Action dated Nov. 23, 2009 for U.S. Appl. No. 11/969,974, filed Jan. 7, 2008, seven pages.
U.S. Non Final Office Action dated Oct. 5, 2016 for U.S. Appl. No. 15/247,419, filed Aug. 25, 2016, eight pages.
U.S. Non Final Office Action dated Oct. 7, 2011 for U.S. Appl. No. 11/964,330, filed Dec. 26, 2007; ten pages.
U.S. Non Final Office Action dated Oct. 23, 2013 for U.S. Appl. No. 13/415,561, filed Mar. 8, 2012, ten pages.
U.S. Non Final Office Action dated Sep. 6, 2016 for U.S. Appl. No. 14/873,842, filed Oct. 2, 2015, seven pages.
U.S. Non Final Office Action dated Sep. 12, 2014 for U.S. Appl. No. 14/154,177, filed Jan. 13, 2014, four pages.
U.S. Non Final Office Action dated Sep. 25, 2017 for U.S. Appl. No. 15/584,405, filed May 2, 2017, eight pages.
U.S. Non Final Office Action with Restriction Requirement dated Mar. 4, 2011 for U.S. Appl. No. 11/830,323, filed Jul. 30, 2007, nine pages.
U.S. Appl. No. 15/810,911, filed Nov. 13, 2017. (Copy not submitted herewith pursuant to the waiver of 37 C.F.R. § 1.98(a)(2)(iii) issued by the Office on Sep. 21, 2004).
U.S. Notice of Allowance dated Apr. 7, 2004 for U.S. Appl. No. 09/905,642, filed Jul. 13, 2001, six pages.
U.S. Notice of Allowance dated Aug. 6, 2015 for U.S. Appl. No. 13/853,656, filed Mar. 29, 2013, seven pages.
U.S. Notice of Allowance dated Aug. 26, 2004 for U.S. Appl. No. 10/050,601, filed Jan. 15, 2002, eight pages.
U.S. Notice of Allowance dated Dec. 10, 2012 for U.S. Appl. No. 11/964,330, filed Dec. 26, 2007, seven pages.
U.S. Notice of Allowance dated Dec. 30, 2016 for U.S. Appl. No. 14/873,842, filed Oct. 2, 2015, eleven pages.
U.S. Notice of Allowance dated Feb. 25, 2010 for U.S. Appl. No. 11/969,974, filed Jan. 7, 2008, four pages.
U.S. Notice of Allowance dated Jan. 2, 2008 for U.S. Appl. No. 10/899,648, filed Jul. 26, 2004, three pages.
U.S. Notice of Allowance dated Jul. 10, 2017 for U.S. Appl. No. 15/247,419, filed Aug. 25, 2016, eight pages.
U.S. Notice of Allowance dated Jun. 25, 2015 for U.S. Appl. No. 12/933,512, filed Nov. 24, 2010 fourteen pages.
U.S. Notice of Allowability dated Mar. 10, 2005 for U.S. Appl. No. 10/050,601, filed Jan. 15, 2002, five pages.
U.S. Notice of Allowance dated Mar. 22, 2013 for U.S. Appl. No. 11/964,330, filed Dec. 26, 2007, eight pages.
U.S. Notice of Allowance dated Mar. 28, 2016 for U.S. Appl. No. 13/853,656, filed Mar. 29, 2013, eight pages.
U.S. Notice of Allowance dated May 18, 2015 for U.S. Appl. No. 13/930,225, filed Jun. 28, 2013, nine pages.
U.S. Notice of Allowance dated Nov. 23, 2015 for U.S. Appl. No. 13/853,656, filed Mar. 29, 2013, seven pages.
U.S. Notice of Allowance dated Oct. 5, 2007 for U.S. Appl. No. 10/899,648, filed Jul. 26, 2004, six pages.
U.S. Notice of Allowance dated Oct. 10, 2014 for U.S. Appl. No. 12/761,462, filed Apr. 16, 2010, ten pages.
U.S. Notice of Allowance dated Sep. 10, 2013 for U.S. Appl. No. 11/412,715, filed Apr. 26, 2006, eight pages.
U.S. Notice of Allowance dated Sep. 14, 2012 for U.S. Appl. No. 11/830,323, filed Jul. 30, 2007, eight pages.
U.S. Restriction Requirement dated Feb. 7, 2019 for U.S. Appl. No. 29/562,795, filed Apr. 28, 2016, seven pages.
Written Opinion of the International Searching Authority dated Aug. 3, 2006 for International Patent Application No. PCT/CA2006/000669, filed on Apr. 27, 2006, eight pages.
Written Opinion of the International Searching Authority dated Dec. 7, 2007 for International Patent Application No. PCT/CA2007/001335, filed on Jul. 30, 2007, four pages.
Australian Notice of Allowance dated Jun. 26, 2019 for Australian Patent Application No. 2016351730 filed on Nov. 10, 2016, three pages.

(56) References Cited

OTHER PUBLICATIONS

European Search Report dated Feb. 18, 2019 for EP Patent Application No. 18178620.3 filed on Jun. 19, 2018, eight pages.
Brazilian Office Action dated Aug. 5, 2019, for Patent Application No. BR1120130229977, filed Mar. 8, 2012, four pages (including English translation).
Canadian Office Action dated Nov. 5, 2019, for Canadian Patent Application No. 3027592, filed on Jun. 14, 2017, four pages.
European Extended Search Report dated May 7, 2019, for Patent Application No. 16863277.6, filed Nov. 10, 2016, seven pages.
Japanese Office Action dated Jul. 12, 2019, for Patent Application No. 2018-51661, filed Nov. 10, 2016, twenty-one pages.
U.S. Non-Final Office Action dated Sep. 27, 2019, for U.S. Appl. No. 29/562,795, filed Apr. 28, 2019, six pages.
U.S. Non-Final Office Action dated Aug. 23, 2019 for U.S. Appl. No. 14/860,687, filed Sep. 21, 2015, fourteen pages.
U.S. Non Final Office Action dated Aug. 21, 2019 for U.S. Appl. No. 15/584,405, filed May 2, 2017, six pages.
U.S. Non-Final Office Action dated Aug. 23, 2019 for U.S. Appl. No. 15/343,034, filed Nov. 3, 2016, eighteen pages.
U.S. Non Final Office Action dated Aug. 23, 2019 for U.S. Appl. No. 15/343,038, filed Nov. 3, 2016, fourteen pages.
Office Action dated Mar. 16, 2020, directed to BR Application No. 112013022997-7; 6 pages.
Notice of Allowance dated Oct. 29, 2019, directed to CA Application No. 2998920; 1 page.
Office Action dated Jul. 6, 2020, directed to CA Application No. 3,009,419; 3 pages.
Notice of Allowance dated Jan. 13, 2020, directed to CN Application No. ZL201710785223.7, 6 pages.
Notification to Pay Restoration Fee for Unity dated Apr. 7, 2020, directed to CN Application No. 201680066060.0, 2 pages.
Office Action dated Jul. 2, 2020, directed to CN Application No. 201680066060.0; 30 pages.
European Extended Search Report dated Jan. 14, 2020, directed to EP Application No. 17812362.6; 8 pages.
European Extended Search Report dated Oct. 16, 2019, directed to EP Application No. 17743524.5; 4 pages.
Decision to Grant dated Jul. 18, 2019, directed to EP Application No. 09819758.5; 2 pages.
International Preliminary Report on Patentability dated Aug. 22, 2019, directed to International Application No. PCT/CA2017/050564; 9 pages.
International Search Report dated Oct. 24, 2017, directed to International Application No. PCT/CA2017/050564; 6 pages.
Invitation to Pay Additional Fees and, where Applicable, Protest Fee dated Jul. 4, 2017, directed to International Application No. PCT/CA2017/050564; 2 pages.
Office Action dated Jan. 10, 2020, directed to JP Application No. 2018-516161; 5 pages.
Notice of Allowance dated Jun. 29, 2020, directed to JP Application No. 2018-516161; 6 pages.
Kolaman, A. et al. (2016). "Amplitude Modulated Video Camera—Light Separation in Dynamic Scenes," IEEE Conference on Computer Vision and Pattern Recognition (CVPR), located at https://www.cv-foundation.org/openaccess/content_cvpr_2016/app/S15-50.pdf last visited on Jun. 8, 2020; 9 pages.
Sensitization (photography), definition from Wikipedia, original language German, 6 pages.
U.S. Ex Parte Quayle Action dated Mar. 23, 2020, directed to U.S. Appl. No. 15/584,405; 5 pages.
U.S. Office Action dated Feb. 4, 2020, directed to U.S. Appl. No. 15/591,909; 13 pages.
U.S. Office Action dated Feb. 7, 2020, directed to U.S. Appl. No. 15/343,038; 16 pages.
U.S. Office Action dated Jul. 25, 2019, directed to U.S. Appl. No. 15/416,876; 13 pages.
U.S. Office Action dated Jul. 15, 2020, directed to U.S. Appl. No. 15/416,876; 20 pages.
U.S. Office Action dated Apr. 3, 2020, directed to U.S. Appl. No. 16/746,539; 15 pages.
U.S. Ex Parte Quayle Action dated Jul. 23, 2020, directed to U.S. Appl. No. 29/724,647; 5 pages.
U.S. Ex Parte Quayle Action dated Jul. 23, 2020, directed to U.S. Appl. No. 29/724,650; 5 pages.
U.S. Ex Parte Quayle Action dated Jul. 23, 2020, directed to U.S. Appl. No. 29/724,651; 5 pages.
Notice of Allowance and Fee(s) Due dated May 19, 2020, directed to U.S. Appl. No. 15/584,405; 9 pages.
U.S. Office Action dated Aug. 6, 2019, directed to U.S. Appl. No. 15/591,909; 9 pages.
U.S. Office Action dated Jan. 16, 2020, directed to U.S. Appl. No. 15/416,876; 14 pages.
U.S. Notice of Allowance and Fee(s) due dated Jul. 13, 2020, directed to U.S. Appl. No. 29/562,795; 7 pages.
U.S. Notice of Allowance and Fee(s) dated Feb. 14, 2020, directed to U.S. Appl. No. 14/860,687; 8 pages.
U.S. Notice of Allowance and Fee(s) dated Feb. 14, 2020, directed to U.S. Appl. No. 15/343,034; 7 pages.
U.S. Notice of Allowance and Fee(s) dated Mar. 12, 2020, directed to U.S. Appl. No. 16/441,493; 8 pages.
U.S. Restriction Requirement dated Jan. 17, 2019, directed to U.S. Appl. No. 15/591,909; 7 pages.
Written Opinion of the International Searching Authority dated Oct. 24, 2017, directed to International Application No. PCT/CA2017/050564; 7 pages.
Decision to Grant a Patent dated Jul. 16, 2021, directed to JP Application No. 2019-540067; 6 pages.
Extended European Search Report dated Oct. 14, 2020, directed to EP Application No. 17895908.6; 8 pages.
Fengler et al., U.S. Advisory Action dated Dec. 20, 2019, directed to U.S. Appl. No. 15/416,876; 5 pages.
Fengler et al., U.S. Advisory Action dated Nov. 2, 2020, directed to U.S. Appl. No. 15/416,876; 5 pages.
Fengler et al., U.S. Notice of Allowance and Fee(s) Due dated Aug. 18, 2020, directed to U.S. Appl. No. 15/623,100; 7 pages.
Fengler et al., U.S. Notice of Allowance and Fee(s) Due dated Dec. 2, 2021, directed to U.S. Appl. No. 17/234,461; 8 pages.
Fengler et al., U.S. Notice of Allowance and Fee(s) Due dated Dec. 4, 2020, directed to U.S. Appl. No. 15/416,876; 9 pages.
First Office Action dated Jul. 30, 2021, directed to JP Application No. 2020-128414; 8 pages.
Intention to Grant dated May 17, 2021, directed to EP Application No. 16 186 321.2; 7 pages.
Moore et al., U.S. Notice of Allowance and Fee(s) due dated Jun. 1, 2021, directed to U.S. Appl. No. 15/591,909; 6 pages.
Moore et al., U.S. Notice of Allowance and Fee(s) due dated Mar. 5, 2019, directed to U.S. Appl. No. 15/348,664; 10 pages.
Moore et al., U.S. Office Action dated Nov. 19, 2020, directed to U.S. Appl. No. 15/591,909; 13 pages.
Moore et al., U.S. Office Action dated Nov. 9, 2021, directed to U.S. Appl. No. 16/933,900; 14 pages.
Moore et al., U.S. Office Action dated Oct. 17, 2019, directed to U.S. Appl. No. 16/441,493; 8 pages.
Murray et al., U.S. Office Action dated Aug. 31, 2020, directed to U.S. Appl. No. 16/746,539; 16 pages.
Notice of Reasons for Refusal dated Feb. 12, 2021, directed to JP Application No. 2019-540067; 13 pages.
Notification to Grant Patent Right for Invention dated Mar. 31, 2021, directed to CN Application No. 201680066060.0; 8 pages.
Office Action dated Jun. 16, 2021, directed to EP Application No. 16 863 277.6; 5 pages.
Office Action dated Nov. 18, 2020, directed to CA Application No. 3,027,592; 3 pages.
Office Action dated Oct. 1, 2021, directed to EP Application No. 17 895 908.6; 4 pages.
Office Action dated Sep. 16, 2020, directed to EP Application No. 16 186 321.2; 4 pages.
U.S. Non-Final Office Action dated Aug. 2, 2019 for U.S. Appl. No. 15/623,100, filed Jun. 14, 2017, twelve pages.
U.S. Non-Final Office Action dated Feb. 5, 2019 for U.S. Appl. No. 15/623,100, filed Jun. 14, 2017, eleven pages.

(56) References Cited

OTHER PUBLICATIONS

U.S. Non-Final Office Action dated May 5, 2020, for U.S. Appl. No. 15/623,100, filed Jun. 14, 2017, twelve pages.

Westwick et al., U.S. Office Action dated Aug. 27, 2020, directed to U.S. Appl. No. 15/343,038; 16 pages.

Westwick et al., U.S. Office Action dated Dec. 16, 2021, directed to U.S. Appl. No. 17/243,002; 19 pages.

Murray et al., U.S. Notice of Allowance and Fee(s) Due dated Dec. 22, 2020, directed to U.S. Appl. No. 16/746,539; 7 pages.

Moore et al., U.S. Advisory Action dated May 19, 2020, directed to U.S. Appl. No. 15/591,909; 3 pages.

Office Action dated Feb. 25, 2022, directed to EP Application No. 18 178 620.3; 4 pages.

Westwick et al., U.S. Office Action dated Nov. 16, 2022, directed to U.S. Appl. No. 17/243,002; 11 pages.

Westwick et al., U.S. Office Action dated May 18, 2022, directed to U.S. Appl. No. 17/243,002; 13 pages.

Moore et al., U.S. Restriction Requirement dated May 3, 2018, directed to U.S. Appl. No. 15/348,664; 5 pages.

Moore et al., U.S. Office Action dated Dec. 13, 2022, directed to U.S. Appl. No. 16/933,900; 15 pages.

Moore et al., U.S. Advisory Action dated Oct. 11, 2022, directed to U.S. Appl. No. 16/933,900; 3 pages.

Moore et al., U.S. Office Action dated May 16, 2022, directed to U.S. Appl. No. 16/933,900; 13 pages.

Office Action dated Dec. 1, 2022, directed to EP Application No. 16 863 277.6; 6 pages.

Notice of Reasons for Refusal dated Apr. 1, 2022, directed to JP Application No. 2020-128414; 11 pages.

Decision of Refusal dated Nov. 11, 2022, directed to JP Application No. 2020-128414; 5 pages.

Intention to Grant dated Feb. 25, 2022, directed to EP Application No. 17 743 524.5; 7 pages.

Fengler et al., U.S. Office Action dated Sep. 14, 2022, directed to U.S. Appl. No. 16/951,684; 14 pages.

Office Action dated Jun. 7, 2022, directed to EP Application No. 17 812 362.6; 5 pages.

Intention to Grant dated Dec. 6, 2022, directed to EP Application No. 17 895 908.6.

Fengler et al., U.S. Restriction Requirement dated Oct. 17, 2018, directed to U.S. Appl. No. 15/623,100; 7 pages.

Notice of Reasons for Refusal dated Sep. 9, 2022, directed to JP Application No. 2021-132340; 8 pages.

\* cited by examiner

| MODE | QUANTITY OF FRAMES FOR GENERATING LOW LIGHT VIDEO OUTPUT | EXPOSURE |
| --- | --- | --- |
| low-motion | high | high |
| moderate-motion | mid | mid |
| high-motion | low | low |

FIG. 4

METHODS AND SYSTEMS FOR ADAPTIVE IMAGING FOR LOW LIGHT SIGNAL ENHANCEMENT IN MEDICAL VISUALIZATION

CROSS-REFERENCE TO RELATED APPLICATIONS

This application is a continuation of U.S. patent application Ser. No. 15/623,100, filed Jun. 14, 2017, which claims the benefit of U.S. Provisional Application No. 62/350,121, filed Jun. 14, 2016, the entire contents of each of which are incorporated herein by reference.

FIELD OF THE INVENTION

The present disclosure relates generally to medical imaging. More specifically, the disclosure relates to adaptive imaging for low light signal enhancement in medical visualization.

BACKGROUND OF THE INVENTION

Imaging technology used in medical visualization (e.g., invasive, minimally-invasive, or non-invasive visualization) can suffer performance degradation under low light conditions. In particular, fluorescence imaging systems used for medical visualization may need to operate with very low emitted signal levels from fluorophores at low concentration, with limited quantum efficiency and/or deeply embedded in the tissue.

Low signal levels are not only problematic in cases of fluorescence imaging, however, but are also known to limit the signal quality of reflected light laparoscopic images which are acquired through small aperture optics (e.g. laparoscopes). The combination of low light signal sources (e.g. fluorescence) and small aperture optics (e.g. laparoscopes) may compound the challenge.

Medical imaging systems (e.g., endoscopic imaging systems for minimally-invasive surgery or open field medical imaging systems) can help provide clinical information for medical practitioners who need to make decisions (e.g. intraoperative or treatment decisions) based on visualization of tissue. In many applications, it is useful for medical imaging systems to provide white light video in combination with another imaging modality (e.g., fluorescence video) substantially simultaneously and in real-time. In particular, in applications for visualizing tissue, the white light video is typically acquired by illuminating the tissue with full visible spectrum light and imaging the illumination light that is reflected from the tissue surface. In typical applications, such white light video ideally maintains a high color fidelity with the image that would be perceived with the normal human eye directly visualizing the same reflected light. Additionally, fluorescence video, for example, may be acquired by illuminating the tissue with excitation light and imaging the fluorescence light that is emitted by excited fluorophores located in the tissue. The white light video (e.g., color video) and the fluorescence video may be merged and presented to the medical practitioner as a single "real-time" video.

There are occasions, however, when there may be a significant disparity between the intensity levels of the reflected illumination light and the fluorescence light. In particular, in many instances, the reflected light image signal may be orders of magnitude larger than the fluorescence image signal. There are some existing options to compensate for such image signal differences (e.g., by adjusting the fluorophore concentration in the tissue, adjusting the intensity of the excitation light, amplifying the electronic fluorescence image signal when the optical fluorescence image signal is transduced at the image sensor or thereafter, etc.). However, these workarounds may prove insufficient for acquiring an adequate fluorescence image signal. In systems that acquire the reflected light image signal and the fluorescence image signal with the same image sensor, providing sufficient compensation for a relatively weak fluorescence image signal becomes particularly challenging.

Furthermore, the reflected light image signal and/or fluorescence image signal may suffer from motion blurring as the result of movement of the imaging system and/or the object being imaged. Such motion blurring, as well as noise in the reflected light and/or fluorescence image signals, may prevent or hamper the visualization of fine details in the fluorescence images.

Thus, it is desirable to have medical imaging systems in which low-intensity image signals, such as for example reflected light image signals and/or fluorescence image signals, can be more effectively visualized and presented to a user.

SUMMARY OF THE INVENTION

According to some embodiments, an adaptive imaging method for generating low light video of an object for medical visualization may include acquiring, with an image acquisition assembly, a sequence of reflected light video frames and/or a sequence of fluorescence video frames depicting the object, assessing relative movement between the image acquisition assembly and the object based on reference video frames that include at least a portion of the acquired sequence of reflected light video frames or a portion of the acquired sequence of fluorescence video frames, adjusting a level of image processing of the reflected light video frames and/or the fluorescence video frames based at least in part on the relative movement (or assessment of relative movement) between the image acquisition assembly and the object, and generating a characteristic low light video output from a quantity of the reflected light video frames and/or a quantity of the fluorescence video frames. In some embodiments, the quantity of the low light video frames for the characteristic low light video output may be based on the adjusted level of image processing of the low light video frames.

Such an adaptive imaging method for use in medical imaging may improve visualization of low light image signals from an object while limiting the introduction of image artifacts during relative movement between the image acquisition assembly and the object. In various embodiments, the method may be used when acquiring video of a single low light image signal (e.g. a reflected white light image signal, or a fluorescence image signal) or when acquiring video of a low light image signal while also acquiring video of a relatively higher intensity image signal (e.g. a low light fluorescence image signal and a higher intensity reflected light image signal). In embodiments that include acquiring video of a relatively higher intensity image signal in addition to a low light image signal, the higher intensity image signal may be used as the source of the reference video frames which may provide for improved assessment of relative motion between the image acquisition assembly and the object. In embodiments that include acquiring video of a single low light image signal, that low light image signal may be used as the source of the reference video frames for assessment of relative motion.

In various embodiments, relative movement between the image acquisition assembly and the object may be assessed by measuring changes in a plurality of the reference video frames, such as change in pixel intensities. For example, change in pixel intensities may be analyzed by determining a representative pixel intensity for each of a plurality of subregions in the plurality of reference video frames, and characterizing the changes in representative pixel intensity for the subregions in the plurality of the reference video frames.

Following the assessment of relative movement between the image acquisition assembly and the object, the level of image processing of the low light video frames may be adjusted by adjusting the quantity of low light video frames from which the characteristic low light video output is generated. In particular, the image processing level may be adjusted based on at least one motion threshold. For instance, adjusting the quantity of low light video frames may include setting the quantity of low light video frames to a first predetermined value if the relative movement (or assessment of relative movement) between the image acquisition assembly and the object is below a first motion threshold, and setting the quantity of low light video frames to a second predetermined value lower than the first predetermined value if the relative movement (or assessment of relative movement) is above the first motion threshold. In some variations, additional motion thresholds may be utilized, such as by setting the quantity of low light video frames to the second predetermined value if the relative movement (or assessment of relative movement) is above the first motion threshold and additionally below a second motion threshold that is higher than the first motion threshold. Additionally, the method may include setting the quantity of low light video frames to a third predetermined value that is lower than the first and second predetermined values if the relative movement (or assessment of relative movement) is above the first and second motion thresholds. In some variations, the quantity of low light video frames may be adjusted or set to a predetermined value by gradually increasing or decreasing the quantity of low light video frames from which the characteristic low light video output is based, over a series of frames of the characteristic fluorescence video output.

The characteristic low light video output may be generated using various image processing steps and based on a quantity of low light video frames associated with the adjusted level of image processing. For example, a frame of the characteristic low light video output may be generated by determining a sum of pixel intensities of the quantity of the low light video frames on a region-by-region basis, and optionally additionally dividing the sum of the pixel intensities by the square root of the quantity of the low light video frames combined to generate the frame of the characteristic low light video output. As another example, a frame of the characteristic low light video output may be generated by averaging pixel intensities of the quantity of low light video frames on a region-by-region basis.

In some variations, the method may additionally or alternatively include performing other actions based on the relative movement (or assessment of relative movement) between the image acquisition assembly and the object, such as adjusting a low light video frame exposure period and/or controlling a timing scheme of the image acquisition assembly, a visible light source illuminating the object, and/or an excitation light source illuminating the object.

The method may further include displaying the characteristic low light video output on a display. Furthermore, the displaying of the low light video output may be generally continuous, as the method in some variations may be performed continuously (e.g., as long as the low light video frames are acquired).

Generally, an adaptive imaging system for generating low light video of an object includes an image acquisition assembly configured to acquire a sequence of low light video frames depicting the object, and a processor. The processor may be configured to assess relative movement between the image acquisition assembly and the object based on a portion of reference video frames, which may include at least a portion of the low light video frames and/or a portion of substantially simultaneously acquired higher intensity light video frames, adjust a level of image processing of the low light video frames based at least in part on the relative movement (or assessment of relative movement) between the image acquisition assembly and the object, and generate a characteristic low light video output from a quantity of the low light video frames, wherein the quantity of the low light video frames is based on the adjusted level of image processing of the low light video frames. The system may further include a visible light source that is configured to emit visible light to illuminate the object, and an excitation light source configured to emit excitation light that causes the object to emit fluorescent light. In some variations, the system may further include a controller that controls a timing scheme for the visible light source, the excitation light source, and the image acquisition assembly based at least in part on the relative movement (or assessment of relative movement) between the image acquisition assembly and the object. The system may include a display that is configured to display the characteristic fluorescence video output and/or the reflected light video frames.

According to an embodiment, an adaptive imaging system for generating low light fluorescence video of an object includes an image acquisition assembly configured to acquire a sequence of reflected light video frames and a sequence of fluorescence video frames depicting the object, and a processor. The processor may be configured to assess relative movement between the image acquisition assembly and the object based on at least a portion of the reflected light video frames, adjust a level of image processing of the fluorescence video frames based at least in part on the relative movement (or assessment of relative movement) between the image acquisition assembly and the object, and generate a characteristic fluorescence video output from a quantity of the fluorescence video frames, wherein the quantity of the fluorescence video frames is based on the adjusted level of image processing of the fluorescence video frames. The system may further include a visible light source that is configured to emit visible light to illuminate the object, and an excitation light source configured to emit excitation light that causes the object to emit fluorescent light. In some variations, the system may further include a controller that controls a timing scheme for the visible light source, the excitation light source, and the image acquisition assembly based at least in part on the relative movement (or assessment of relative movement) between the image acquisition assembly and the object. The system may include a display that is configured to display the characteristic fluorescence video output and/or the reflected light video frames.

The processor of the adaptive imaging system may be configured to assess relative movement between the image acquisition assembly and the object by measuring changes in pixel intensities in a plurality of the reference video frames. Based on this relative movement (or assessment of relative movement), the processor may be configured to adjust the level of image processing of the low light video frames, such as by adjusting the quantity of low light video frames from which the characteristic low light video output is generated. More specifically, the processor may set the quantity of low light video frames to a first predetermined value if the relative movement (or assessment of relative movement) between the image acquisition assembly and object is below a first motion threshold, and set the quantity of low light video frames to a second predetermined value if the relative movement (or assessment of relative movement) between the image acquisition assembly and object is above the first motion threshold, wherein the second predetermined value is lower than the first predetermined value. Additionally, the processor may set the quantity of low light video frames to the second predetermined value if the relative movement (or assessment of relative movement) between the image acquisition assembly and the object is above the first motion threshold and below a second motion threshold higher than the first motion threshold and set the quantity of low light video frames to a third predetermined value if the relative movement (or assessment of relative movement) between the image acquisition assembly and the object is above the first and second motion thresholds, the third predetermined value being lower than the first and second predetermined values. In some variations, the processor may adjust or set the quantity of low light video frames to a predetermined value by gradually increasing or decreasing the quantity of low light video frames from which the characteristic low light video output is based, over a series of frames of the characteristic low light video output.

The processor may be configured to generate the characteristic low light video output in one or more of various manners, such as by determining a sum of pixel intensities of the quantity of the low light video frames on a region-by-region basis and optionally dividing the sum of pixel intensities by the square root of the quantity of low light video frames, or averaging pixel intensities of the quantity of the low light video frames on a region-by-region basis.

Furthermore, in some variations, some or all of the components of the adaptive imaging system may be combined or integrated with other technologies. For example, the adaptive imaging system may further include an image stabilization system that is implemented in hardware, software, or a combination thereof. As another example, the adaptive imaging system described herein may be embodied in an endoscopic imaging system.

According to some embodiments, an adaptive imaging method for generating fluorescence video of an object, includes acquiring, with an image acquisition assembly, a sequence of reflected light video frames and a sequence of fluorescence video frames depicting the object, assessing relative movement between the image acquisition assembly and the object based on at least a portion of the acquired sequence of reflected light video frames, adjusting a level of image processing of the fluorescence video frames based at least in part on the relative movement between the image acquisition assembly and the object, and generating a characteristic fluorescence video output from a quantity of the fluorescence video frames, wherein the quantity of the fluorescence video frames is based on the adjusted level of image processing of the fluorescence video frames.

In any of these embodiments, assessing relative movement between the image acquisition assembly and the object may include measuring changes in pixel intensities in a plurality of the reflected light video frames. In any of these embodiments, assessing relative movement between the image acquisition assembly and the object may include determining a representative pixel intensity for each of a plurality of subregions in the plurality of reflected light video frames, and characterizing the changes in representative pixel intensity for the subregions in the plurality of the reflected light video frames.

In any of these embodiments, adjusting the level of image processing of the fluorescence video frames may include adjusting the quantity of fluorescence video frames from which the characteristic fluorescence video output is generated. In any of these embodiments, adjusting the quantity of fluorescence video frames may include setting the quantity of fluorescence video frames to a first predetermined value if the relative movement between the image acquisition assembly and the object is below a first motion threshold. In any of these embodiments, setting the quantity of fluorescence video frames to the first predetermined value may include gradually increasing or decreasing the quantity of fluorescence video frames to the first predetermined value over a series of frames of the characteristic fluorescence video output.

In any of these embodiments, adjusting the quantity of fluorescence video frames may include setting the quantity of fluorescence video frames to a second predetermined value if the relative movement between the image acquisition assembly and the object is above the first motion threshold, the second predetermined value being lower than the first predetermined value. In any of these embodiments, setting the quantity of fluorescence video frames to the second predetermined value may include gradually increasing or decreasing the quantity of fluorescence video frames to the second predetermined value over a series of frames of the characteristic fluorescence video output.

In any of these embodiments, adjusting the quantity of fluorescence video frames may include setting the quantity of fluorescence video frames to the second predetermined value if the relative movement between the image acquisition assembly and the object is above the first motion threshold and below a second motion threshold higher than the first motion threshold, and setting the quantity of fluorescence video frames to a third predetermined value, if the relative movement between the image acquisition assembly and the object is above the first and second motion thresholds, the third predetermined value being lower than the first and second predetermined values.

In any of these embodiments, setting the quantity of fluorescence video frames to the third predetermined value may include gradually increasing or decreasing the quantity of fluorescence video frames to the third predetermined value over a series of frames of the characteristic fluorescence video output. In any of these embodiments, adjusting the quantity of fluorescence video frames may include gradually increasing or decreasing the quantity of fluorescence video frames toward a predetermined value over a series of frames of the characteristic fluorescence video output. In any of these embodiments, generating the characteristic fluorescence video output may include determining a sum of pixel intensities of the quantity of the fluorescence video frames on a region-by-region basis.

In any of these embodiments, generating the characteristic fluorescence video output may further include dividing the sum of pixel intensities by the square root of the quantity of the fluorescence video frames. In any of these embodiments, generating the characteristic fluorescence video output from the quantity of the fluorescence video frames may include averaging pixel intensities of the quantity of the fluorescence video frames on a region-by-region basis. In any of these embodiments, the method may further include adjusting a fluorescence video frame exposure period based at least in part on the relative movement between the image acquisition assembly and the object.

In any of these embodiments, the method may further include displaying at least one of the characteristic fluorescence video output and the reflected light video frames on a display. In any of these embodiments, the method may further include controlling a timing scheme of a visible light source illuminating the object, an excitation light source illuminating the object, and the image acquisition assembly based at least in part on the relative movement between the image acquisition assembly and the object. In any of these embodiments, the method may be performed continuously.

According to some embodiments, an adaptive imaging system for generating fluorescence video of an object, includes an image acquisition assembly configured to acquire a sequence of reflected light video frames and a sequence of fluorescence video frames depicting the object, and a processor configured to assess relative movement between the image acquisition assembly and the object based on at least a portion of the reflected light video frames, adjust a level of image processing of the fluorescence video frames based at least in part on the assessed relative movement between the image acquisition assembly and the object, and generate a characteristic fluorescence video output from a quantity of the fluorescence video frames, wherein the quantity of the fluorescence video frames is based on the adjusted level of image processing of the fluorescence video frames.

In any of these embodiments, the system may further include a visible light source configured to emit visible light to illuminate the object, and an excitation light source configured to emit excitation light that causes the object to emit fluorescent light. In any of these embodiments, the system may further include a controller that controls a timing scheme for the visible light source, the excitation light source, and the image acquisition assembly based at least in part on the relative movement between the image acquisition assembly and the object. In any of these embodiments, the processor may be configured to assess relative movement by measuring changes in pixel intensities in a plurality of the reflected light video frames.

In any of these embodiments, the processor may be configured to adjust the level of image processing of the fluorescence video frames by adjusting the quantity of fluorescence video frames from which the characteristic fluorescence video output is generated. In any of these embodiments, the processor may be configured to adjust the quantity of fluorescence video frames by setting the quantity of fluorescence video frames to a first predetermined value if the relative movement between the image acquisition assembly and object is below a first motion threshold, and setting the quantity of fluorescence video frames to a second predetermined value if the relative movement between the image acquisition assembly and object is above the first motion threshold, the second predetermined value being lower than the first predetermined value.

In any of these embodiments, the processor may be configured to adjust the quantity of fluorescence video frames by setting the quantity of fluorescence video frames to the second predetermined value, if the relative movement between the image acquisition assembly and the object is above the first motion threshold and below a second motion threshold higher than the first motion threshold, and setting the quantity of fluorescence video frames to a third predetermined value, if the relative movement between the image acquisition assembly and the object is above the first and second motion thresholds, the third predetermined value being lower than the first and second predetermined values.

In any of these embodiments, the processor may be configured to adjust the quantity of fluorescence video frames by gradually increasing or decreasing the quantity of fluorescence video frames toward a predetermined value over a series of frames of the characteristic fluorescence video output. In any of these embodiments, the processor may be configured to generate the characteristic fluorescence video output by performing: (i) determining a sum of pixel intensities of the quantity of the fluorescence video frames on a region-by-region basis, (ii) determining a sum of pixel intensities of the quantity of the fluorescence video frames on a region-by-region basis and dividing the sum of pixel intensities by the square root of the quantity of fluorescence video frames, (iii) averaging pixel intensities of the quantity of the fluorescence video frames on a region-by-region basis, or (iv) a combination thereof.

In any of these embodiments, the system may further include a display configured to display at least one of the characteristic fluorescence video output and the reflected light video frames. In any of these embodiments, at least a portion of the imaging system may be embodied in an endoscopic imaging system. In any of these embodiments, the system may further include an image stabilization system implemented in hardware, software, or a combination thereof.

According to some embodiments, a computer-implemented, adaptive imaging method for generating fluorescence video of an object, includes receiving a sequence of reflected light video frames and a sequence of fluorescence video frames depicting the object, wherein the reflected light video frames and fluorescence video frames are acquired by an image acquisition assembly, assessing relative movement between the image acquisition assembly and the object based on at least a portion of the reflected light video frames, adjusting a level of image processing of the fluorescence video frames based at least in part on the relative movement between the image acquisition assembly and the object, and generating a characteristic fluorescence video output from a quantity of the fluorescence video frames, wherein the quantity of the fluorescence video frames is based on the adjusted level of image processing of the fluorescence video frames.

According to some embodiments, an adaptive imaging method for generating fluorescence video of an object, includes acquiring, with an image acquisition assembly, a sequence of reflected light video frames depicting the object, assessing relative movement between the image acquisition assembly and the object based on at least a portion of the acquired sequence of reflected light video frames, adjusting a fluorescence video frame exposure period based at least in part on the relative movement between the image acquisition assembly and the object, and acquiring a sequence of fluorescence video frames using the adjusted fluorescence video frame exposure period.

According to some embodiments, an adaptive imaging method for generating enhanced low-intensity light video of an object for medical visualization, includes acquiring, with an image acquisition assembly, a sequence of low light video frames depicting the object, receiving a sequence of reference video frames, assessing relative movement between the image acquisition assembly and the object based on the reference video frames, adjusting a level of image processing of the low light video frames based at least in part on the relative movement between the image acquisition assembly and the object, and generating a characteristic low light video output from a quantity of the low light video frames, wherein the quantity of the low light video frames is based on the adjusted level of image processing of the low light video frames.

According to some embodiments, a kit for imaging an object may include a fluorescence imaging agent and the system of any one of the above embodiments.

According to some embodiments, a fluorescence imaging agent may include a fluorescence imaging agent for use with the system of any one of the above embodiments, the method of any one of the above embodiments, or the kit of any one of the above embodiments.

In any of these embodiments, imaging an object may include imaging an object during blood flow imaging, tissue perfusion imaging, lymphatic imaging, or a combination thereof.

In any of these embodiments, blood flow imaging, tissue perfusion imaging, and/or lymphatic imaging may include blood flow imaging, tissue perfusion imaging, and/or lymphatic imaging during an invasive surgical procedure, a minimally invasive surgical procedure, or during a non-invasive surgical procedure.

In any of these embodiments, the invasive surgical procedure may include a cardiac-related surgical procedure, or a reconstructive surgical procedure.

In any of these embodiments, the cardiac-related surgical procedure may include a cardiac coronary artery bypass graft (CABG) procedure.

In any of these embodiments, the CABG procedure may include on pump or off pump.

In any of these embodiments, the non-invasive surgical procedure may include a wound care procedure.

In any of these embodiments, the lymphatic imaging may include identification of a lymph node, lymph node drainage, lymphatic mapping, or a combination thereof.

In any of these embodiments, the lymphatic imaging may relate to the female reproductive system.

BRIEF DESCRIPTION OF THE DRAWINGS

Features will become apparent to those of ordinary skill in the art by describing in detail exemplary embodiments with reference to the attached drawings in which:

FIG. 4 is a table summarizing exemplary characteristics of imaging modes in one variation of an adaptive imaging method for generating low light video of an object;

DETAILED DESCRIPTION OF THE INVENTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 10:
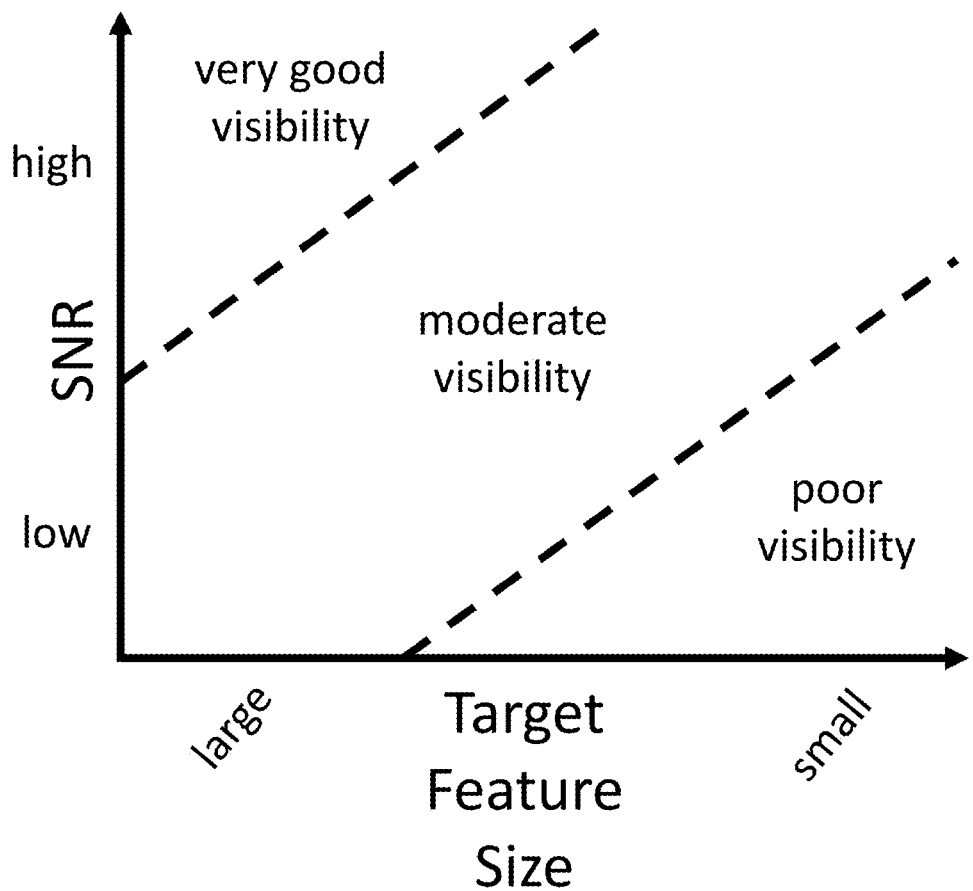
FIG. 10 is an illustrative diagram of a range of image quality regimes.

In various embodiments, with reference to a particular use environment (e.g., imaging modality, clinical application, or a combination thereof), "low light video" comprises video wherein the signal to noise ratio (SNR) of the imaged light is relatively low enough such that it may cause image noise to interfere with the ability to clearly visualize a target feature in the image. In various embodiments, the minimum size of a clinically important target feature may vary according to the use environment, with a lower minimum target feature size generally requiring a higher SNR to yield a given level of feature visibility than a higher minimum target feature size. As shown in FIG. 10, varying video image quality regimes with very good visibility of a target feature, moderate visibility, and poor visibility may generally be expected to depend on the SNR, the minimum target feature size for a given use environment or a combination thereof. For example, the methods and systems for adaptive imaging for low light signal enhancement, as described herein in accordance with the various embodiments, may facilitate imaging low light video within the moderate visibility or poor visibility image quality regimes. According to some embodiments, the methods and systems may allow for user input to determine whether to apply the adaptive imaging for a given use environment and an anticipated associated image quality regime. In some variations, the adaptive imaging may be activated or deactivated automatically depending on the user-indicated use environment.

Generally, the methods and systems described herein may be used to generate real-time enhanced low light videos (including, for example, reflected light videos and/or fluorescence videos), such as for use in applications including imaging of tissue (e.g., during endoscopic examinations, surgical procedures (e.g., minimally invasive), open field imaging, and/or other imaging performed with medical imaging systems, including handheld imaging systems). In some embodiments, the low light video may comprise reflected light video that may be based on visible spectrum light that illuminates and subsequently is reflected from tissue to be visualized. In some embodiments, the low light video may comprise fluorescence light video that may be based on fluorescent light that is emitted by fluorophores located in the tissue to be visualized, after the fluorophores are excited by excitation spectrum light. In some embodiments, a higher intensity light video may be acquired in addition to the low light video. In particular, the adaptive imaging methods and systems described herein may be configured to enhance a low light image signal such as by compensating for signal noise and/or for motion blur. In some embodiments, the adaptive imaging methods and systems described herein may be configured to compensate for a low light image signal that is relatively low-intensity compared to a high-intensity reference image signal, and/or compensate for motion blur and/or signal noise.

Adaptive Imaging Method

Figure 1A:
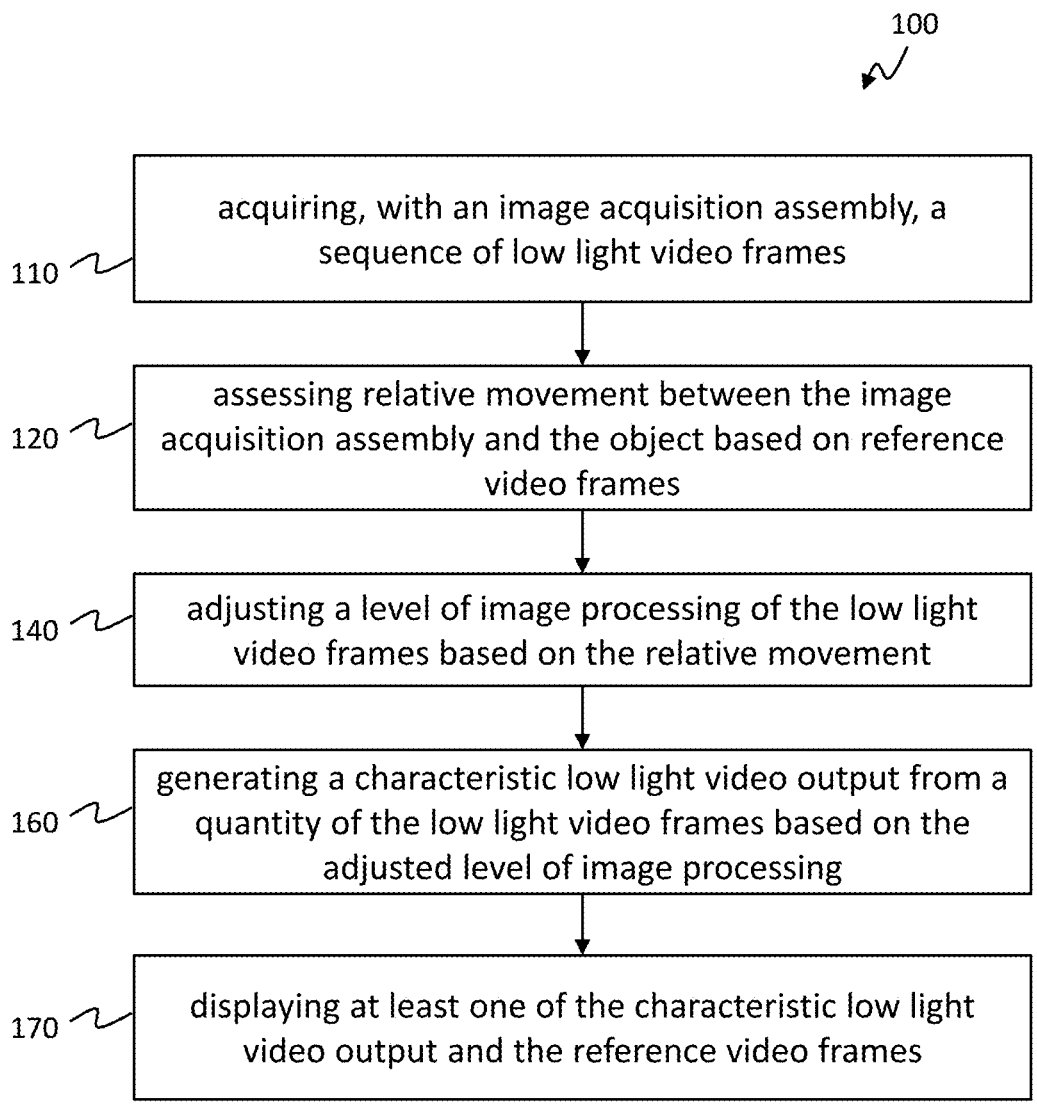
FIG. 1A is an illustrative schematic of an adaptive imaging method for generating low light video of an object according to an embodiment.

FIG. 1 illustrates a schematic of an adaptive imaging method for low light signal enhancement in medical imaging according to an embodiment. As shown in FIG. 1A, an example of an adaptive imaging method 100 for generating fluorescence video of an object may include: acquiring, with an image acquisition assembly, a sequence of low light video depicting the object 110; assessing relative movement between the image acquisition assembly and the object 120 based on reference video frames comprising at least a portion of the acquired sequence of low light video frames and/or a portion of a substantially simultaneously acquired sequence of higher intensity light video frames; adjusting a level of image processing of the low light video frames 140 based at least in part on the relative movement between the image acquisition assembly and the object; and generating a characteristic low light video output from a quantity of the low light video frames 160, wherein the quantity of the low light video frames is based on the adjusted level of image processing of the low light video frames.

In another variation, an adaptive imaging method for generating fluorescence video of an object may include: acquiring, with an image acquisition assembly, a sequence of reflected light video frames and a sequence of fluorescence video frames depicting the object; assessing relative movement between the image acquisition assembly and the object based on at least a portion of the acquired sequence of reflected light video frames; adjusting a level of image processing of the fluorescence video frames based at least in part on the relative movement between the image acquisition assembly and the object; and generating a characteristic fluorescence video output from a quantity of the fluorescence video frames, wherein the quantity of the fluorescence video frames is based on the adjusted level of image processing of the fluorescence video frames.

In some embodiments, the method may include controlling a timing scheme of one or more light sources and the image acquisition assembly, based at least in part on the relative movement between the image acquisition assembly and the object. The method may further include displaying at least one of the characteristic low light video output (e.g., fluorescence video output) and the reference video frames 170 (e.g., reflected light video frames) on a display. In some variations, the method may be performed continuously throughout acquisition of the low light video frames (e.g., reflected light video frames, or fluorescence video frames).

Figure 1B:
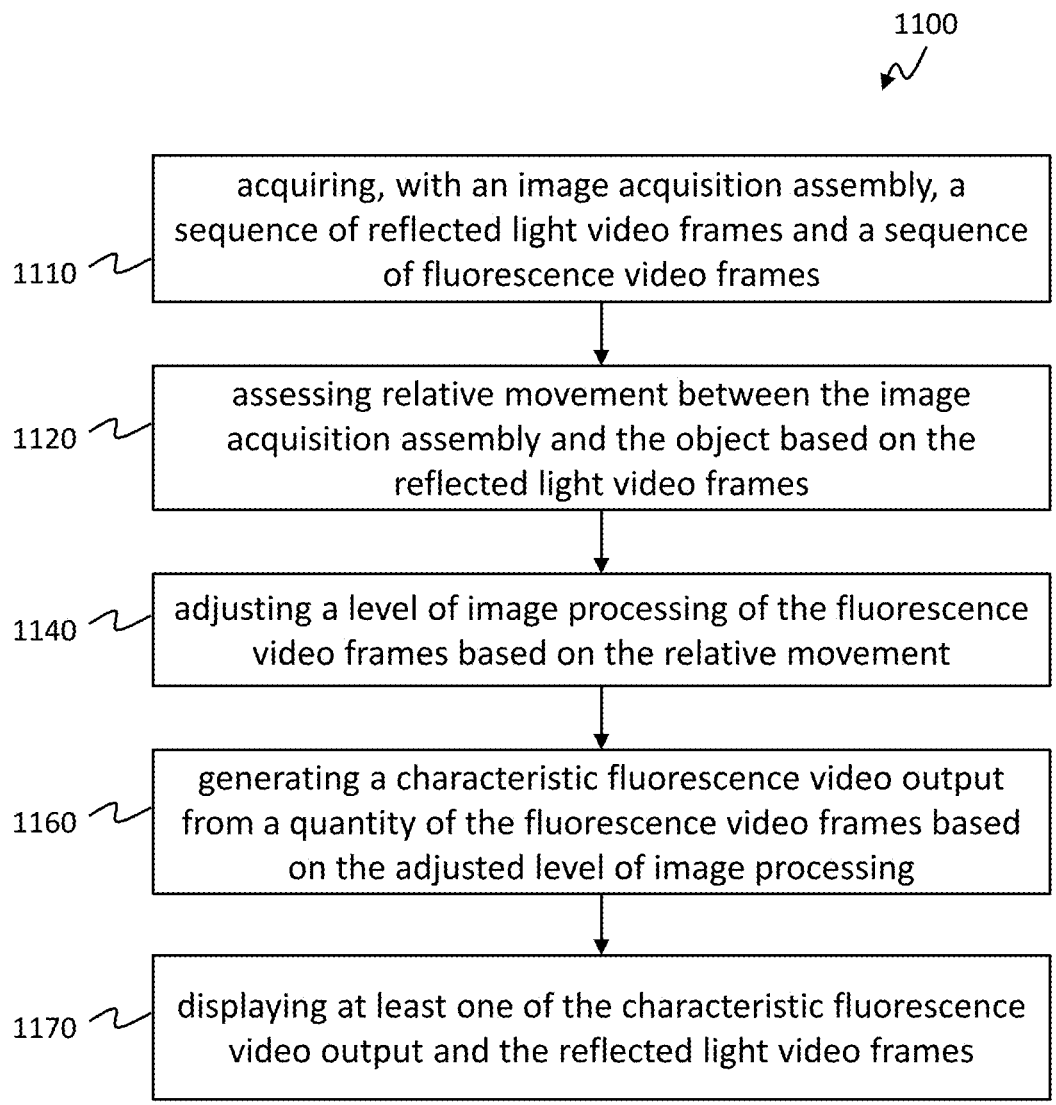
FIG. 1B is an illustrative schematic of an adaptive imaging method for generating fluorescence video of an object according to an embodiment.

In an embodiment, as shown in FIG. 1B, an example of an adaptive imaging method 1100 for generating fluorescence video of an object may include: acquiring, with an image acquisition assembly, a sequence of reflected light video frames and a sequence of fluorescence video frames depicting the object 1110; assessing relative movement between the image acquisition assembly and the object 1120 based on at least a portion of the acquired sequence of reflected light video frames; adjusting a level of image processing of the fluorescence video frames 1140 based at least in part on the relative movement between the image acquisition assembly and the object; and generating a characteristic fluorescence video output from a quantity of the fluorescence video frames 1160, wherein the quantity of the fluorescence video frames is based on the adjusted level of image processing of the fluorescence video frames. The method may include controlling a timing scheme of one or more light sources and the image acquisition assembly, based at least in part on the relative movement between the image acquisition assembly and the object. The method may further include displaying at least one of the characteristic fluorescence video output and the reflected light video frames 1170 on a display. In some variations, the method may be performed continuously throughout acquisition of the reflected light video frames and fluorescence video frames.

Acquiring Image Sequences

According to an embodiment, the method may include acquiring a sequence of low light video frames depicting the object to be visualized (e.g., tissue), with the use of an image acquisition assembly including at least one image sensor. Such acquisition may include illuminating the object with illumination light (e.g., light in the visible light spectrum) and/or excitation light. The low light video frames may comprise reflected light video frames that may be obtained with the image acquisition assembly receiving illumination light that is reflected from the tissue. The reflected light video frames may include color images and/or grayscale images, depending on the kind of image sensors in the image acquisition assembly, as further described below. Additionally, or alternatively, the low light video frames may comprise fluorescence video frames that may be obtained with the image acquisition assembly receiving fluorescence light that is emitted from intrinsic and/or extrinsic fluorophores (e.g., a fluorescence imaging agent introduced into the object) that are present in the tissue and excited by the excitation light. In addition to the sequence of low light video frames, the method may include acquiring a sequence of reference video frames comprising higher light intensity video frames.

According to an embodiment, the method may include acquiring sequences of reflected light video frames and fluorescence video frames depicting the object to be visualized (e.g., tissue), with the use of an image acquisition assembly including at least one image sensor. Such acquisition may include illuminating the object with illumination light (e.g., light in the visible light spectrum) and excitation light. Reflected light video frames that may be obtained with the image acquisition assembly receiving illumination light that is reflected from the tissue. The reflected light video frames may include color images and/or grayscale images, depending on the kind of image sensors in the image acquisition assembly, as further described below. Fluorescence video frames that may be obtained with the image acquisition assembly receiving fluorescence light that is emitted from intrinsic and/or extrinsic fluorophores (e.g., a fluorescence imaging agent introduced into the object) that are present in the tissue and excited by the excitation light.

In some variations, the low light video frames may be fluorescence video frames and the reference video frames may be higher light intensity reflected light video frames. The reflected light video frames and the fluorescence video frames may be acquired substantially in parallel or simultaneously, and in real-time. For example, the reflected light image signal and the fluorescence image signal may be acquired with respective image sensors. As another example, in variations in which the same single image sensor is used to acquire both reflected light video frames and fluorescence video frames, the acquisition of video frames may be performed according to a timing scheme. This timing scheme may enable separation of the image signal associated with the reflected light and the image signal associated with the fluorescence emission light. In particular, the timing scheme may involve illuminating the object with illumination light and excitation light according to a pulsing scheme, and processing the reflected light image signal and fluorescence image signal with a processing scheme, wherein the processing scheme is synchronized and matched to the pulsing scheme (e.g., via a controller) to enable separation of the two image signals in a multiplexed manner. Examples of such pulsing and image processing schemes have been described in U.S. Pat. No. 9,173,554, filed on Mar. 18, 2009 and titled "IMAGING SYSTEM FOR COMBINED FULL-COLOR REFLECTANCE AND NEAR-INFRARED IMAGING," the contents of which are incorporated in their entirety by this reference. However, other suitable pulsing and image processing schemes may be used to acquire reflected light video frames and fluorescence video frames simultaneously.

In an embodiment, as the low light video frames and/or the reference video frames are acquired, at least a portion of them may be stored (e.g., in a memory unit) for record-keeping purposes and/or retrieval for analysis during other aspects of the method, as described below.

In an embodiment, as the reflected light video frames and the fluorescence video frames are acquired, at least a portion of them may be stored (e.g., in a memory unit) for record-keeping purposes and/or retrieval for analysis during other aspects of the method, as described below.

Assessing Relative Movement

According to some embodiments, the method may include assessing the relative movement between the image acquisition assembly and the object based on the reference video frames 120. The assessment of such relative movement may, for example, provide a parameter, where the parameter can be used to determine the manner in which the low light video frames should be processed and/or acquired in order to appropriately increase sensitivity or reduce noise in the low light imaging. The relative movement may result, for example, from unsteady handling of the image acquisition assembly (e.g., when the image acquisition assembly is located in a handheld laparoscope or other handheld imaging system), or movement of a patient being imaged. The relative movement may be better represented in the reference video frames, since the reference video frames may preferably be acquired in real-time with relatively higher light intensity and relatively low latency. In some variations, however, a higher light intensity video signal may not be available and the reference video frames may instead comprise frames of the acquired low light video frames.

According to some embodiments, the method may include assessing the relative movement between the image acquisition assembly and the object based on the reflected light video frames. The assessment of such relative movement may, for example, provide a parameter, where the parameter can be used to determine the manner in which the fluorescence video frames should be processed and/or acquired in order to appropriately increase sensitivity or reduce noise in the fluorescence imaging. The relative movement may be better represented in the reflected light video frames, since the reflected light video frames may be acquired in real-time with relatively higher light intensity and relatively low latency.

In some variations, assessing relative movement between the image acquisition assembly and the object 120 may include measuring changes in pixel intensities in a plurality of the reference video frames. The pixel intensities in the reference video frames may be measured, for example, from luminance grayscale images based on the reference video frames. In variations in which the reference video frames are color images or white light images (e.g., acquired with one or more image sensors with a color filter array such as a Bayer pattern filter), the method may include generating luminance grayscale images from the luminance (brightness) components of the reference video frames. In variations in which the reference video frames are acquired with a non-color image sensor (e.g., an image sensor without a color filter array), the reference video frames may need not to be converted into a separate luminance image.

In some variations, assessing relative movement between the image acquisition assembly and the object may include measuring changes in pixel intensities in a plurality of the reflected light video frames. The pixel intensities in the reflected light video frames may be measured, for example, from luminance grayscale images based on the reflected light video frames. In variations in which the reflected light video frames are color images or white light images (e.g., acquired with one or more image sensors with a color filter array such as a Bayer pattern filter), the method may include generating luminance grayscale images from the luminance (brightness) components of the reflected light video frames. In variations in which the reflected light video frames are acquired with a non-color image sensor (e.g., an image sensor without a color filter array), the reflected light video frames may need not to be converted into a separate luminance image.

Figure 2A:
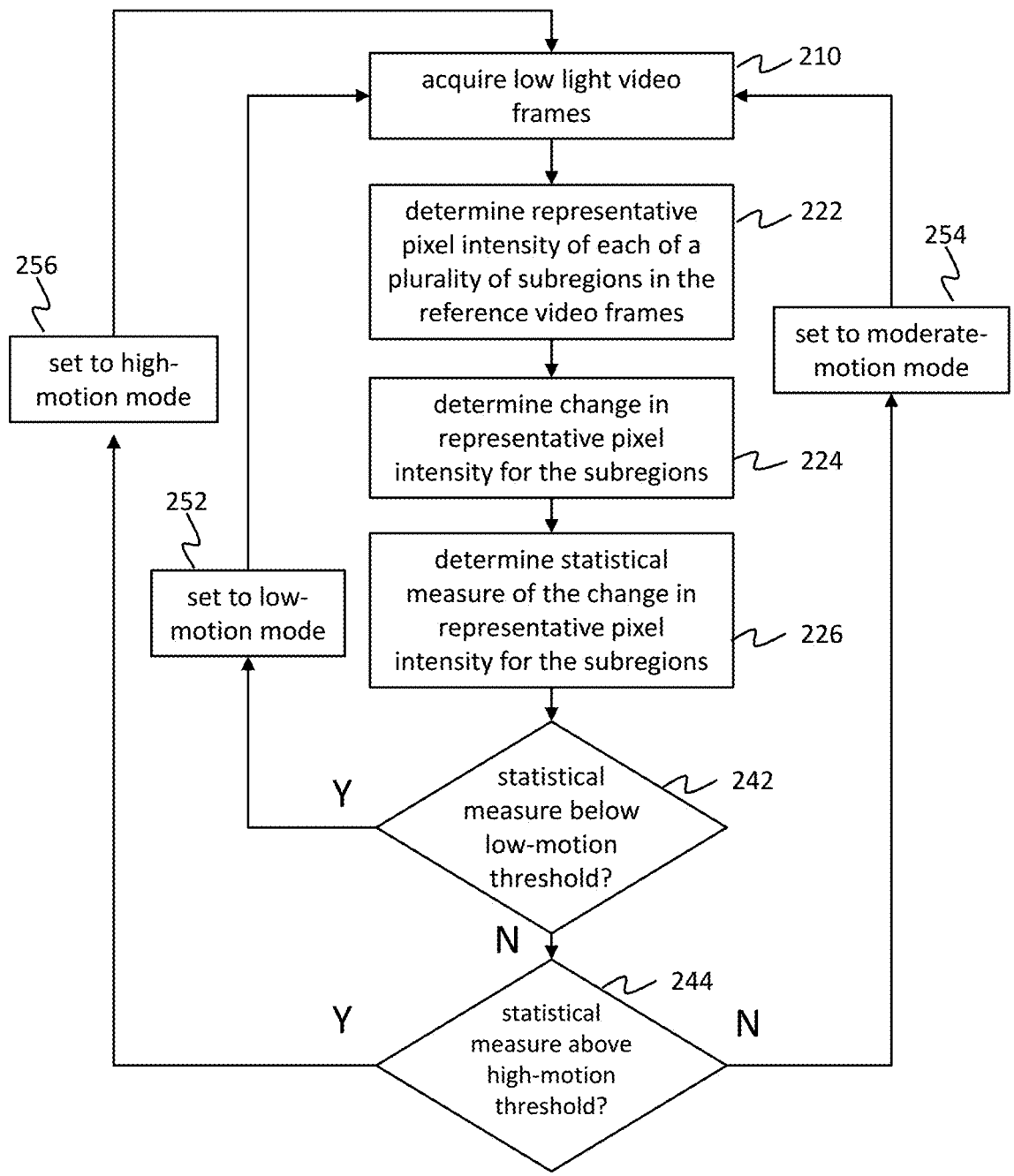
FIG. 2A is an illustrative flowchart of one variation of an adaptive imaging method for generating low light video of an object according to an embodiment.
Figure 3:
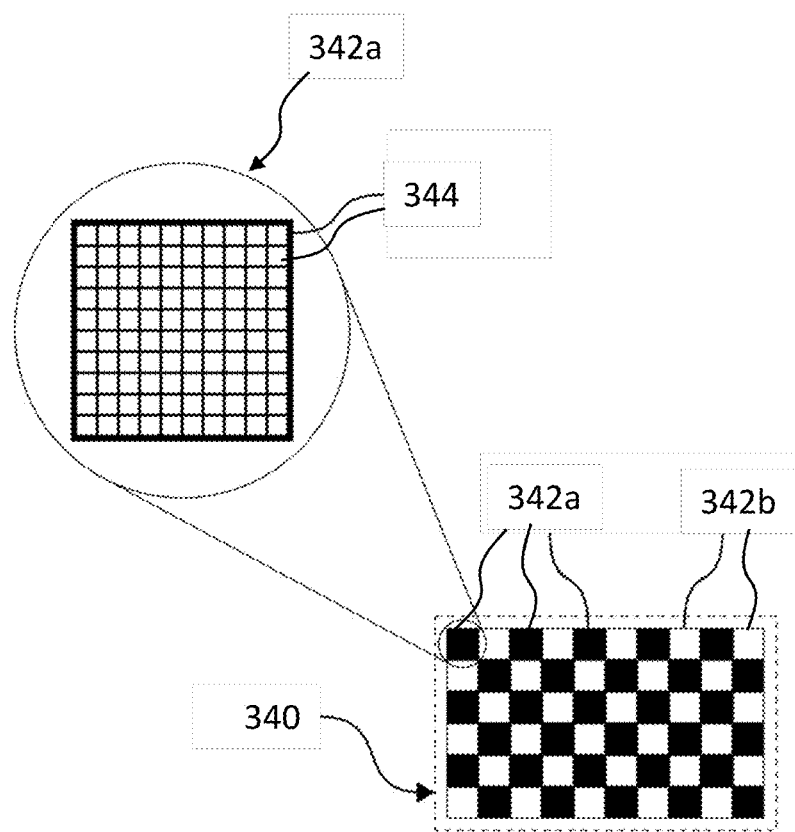
FIG. 3 is an illustrative schematic of a subsampled image sensor used in one variation of an adaptive imaging method for generating low light video of an object according to an embodiment.

In an exemplary embodiment shown in FIG. 2A, after acquiring low light video frames (210), assessing the relative movement may include determining a representative pixel intensity for one or more subregions in the reference video frames (222), wherein the reference video frames may comprise at least a portion of the low light video frames and/or a portion of substantially simultaneously acquired higher intensity light video frames. In particular, each reference video frame may include a plurality of subregions, where each subregion includes a group of pixels. For example, as shown in FIG. 3, a video frame 340 may include subregions 342a and 342b, where each subregion 342a or 342b includes a group of pixels 344 arranged in a cluster (e.g., 1024 pixels arranged in a 32×32 grid, or 100 pixels arranged in a 10×10 grid as depicted in FIG. 3, etc.). The representative pixel intensity for each of one or more subregions may be calculated as the average (e.g., mean) intensity of the group of pixels in the subregion, median intensity of the group of pixels in the subregion, or other manner that is characteristic of the overall pixel intensity of the subregion. Utilizing a representative pixel intensity for multi-pixel subregions may reduce computational complexity of the motion assessment and/or reduce the sensitivity to the resolution of the motion assessment. Alternatively, one or more of the subregions may include a single individual pixel, such as in instances in which computational complexity is less of a concern or more detailed/higher resolution intensity information is desired for assessing relative movement.

In an embodiment, after acquiring reflected light and fluorescence video frames, assessing the relative movement may include determining a representative pixel intensity for one or more subregions in the reflected light video frames. In particular, each reflected light video frame may include a plurality of subregions, where each subregion includes a group of pixels as described herein.

Figure 2B:
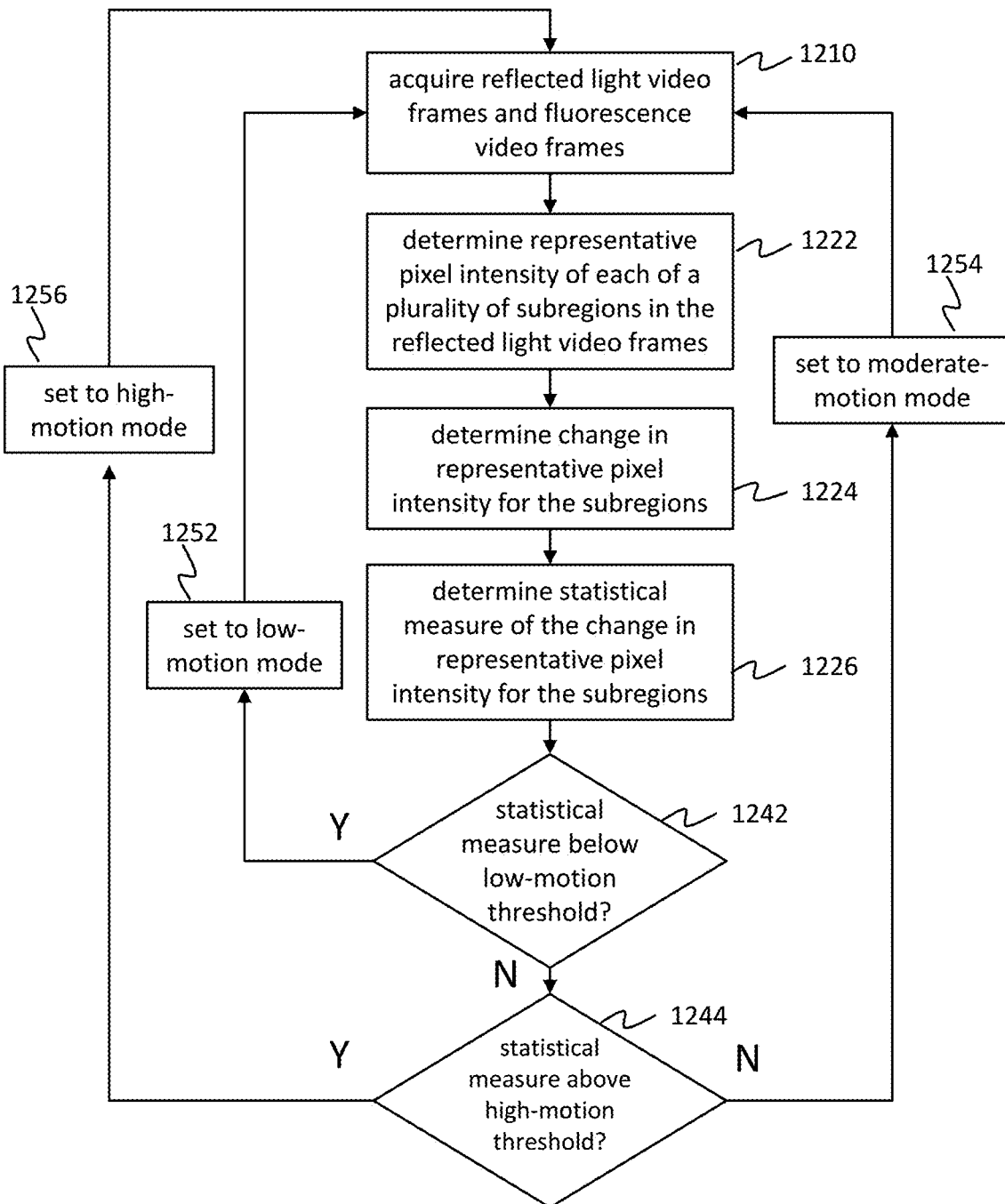
FIG. 2B is an illustrative flowchart of one variation of an adaptive imaging method for generating fluorescence video of an object according to an embodiment.

In an exemplary embodiment shown in FIG. 2B, after acquiring reference reflected light video frames and low light fluorescence video frames (1210), assessing the relative movement may include determining a representative pixel intensity for one or more subregions in the reflected light video frames (1222). In particular, each reflected light video frame may include a plurality of subregions, where each subregion includes a group of pixels. For example, as shown in FIG. 3, a video frame 340 may include subregions 342a and 342b, where each subregion 342a or 342b includes a group of pixels 344 arranged in a cluster (e.g., 1024 pixels arranged in a 32×32 grid, or 100 pixels arranged in a 10×10 grid as depicted in FIG. 3, etc.). The representative pixel intensity for each of one or more subregions may be calculated as the average (e.g., mean) intensity of the group of pixels in the subregion, median intensity of the group of pixels in the subregion, or other manner that is characteristic of the overall pixel intensity of the subregion. Utilizing a representative pixel intensity for multi-pixel subregions may reduce computational complexity of the motion assessment and/or reduce the sensitivity to the resolution of the motion assessment. Alternatively, one or more of the subregions may include a single individual pixel, such as in instances in which computational complexity is less of a concern or more detailed/higher resolution intensity information is desired for assessing relative movement. Although FIG. 3 depicts rectangular or grid-like subregions, the subregions may have any suitable shape. The subregions may be substantially identical in size and shape, though in some variations, some subregions may be different in size or shape. For example, if some areas of the video frames are identified as more important (e.g., depict an object of interest instead of background) and it is desirable to assess relative motion based on more detailed information for those particularly important areas, subregions in the particularly important areas may be smaller than less-important regions. All of the subregions may be considered in the assessment of relative motion or, alternatively, only a subset of one or more of the subregions may be considered, for example to reduce computational complexity and/or to focus assessment of relative motion on a particular region of interest. For example, in some variations, one of the subsets of alternating subregions 342a and 342b, may be omitted from consideration in the assessment of relative motion.

In an embodiment, assessing the relative movement may further include characterizing the change in the representative pixel intensity for the subregions in the reference video frames. In an embodiment, assessing the relative movement may further include characterizing the change in the representative pixel intensity for the subregions in the reflected light video frames. The characterization may be quantitative (e.g., a numerical value describing the magnitude of relative movement between the image acquisition assembly and the object). At least two sequential video frames may be analyzed (e.g., to characterize how the representative pixel intensities for the subregions have changed between an immediately prior video frame to a current frame, or between non-adjacent frames representing endpoints of a multi-frame time period of interest). For instance, in the exemplary embodiment shown in FIG. 2A, assessing the relative movement may further include determining the change in representative pixel intensity for the subregions 224 and determining a statistical measure of the change in representative pixel intensity for the subregions 226. The statistical measure is representative of the assessed relative motion between the image acquisition assembly and the object. For example, to characterize the relative movement of the image acquisition assembly and object over the course of two adjacent reference video frames (or two adjacent reflected light video frames), step 224 may include determining the difference between the representative pixel intensity for a subregion in a current video frame and the representative pixel intensity for the same subregion in a previous video frame, and repeating this determination for all considered subregions. Subsequently, determining a statistical measure 226 may include, for example, calculating the standard deviation of the differences determined in block 224. As another example, determining a statistical measure 226 may include calculating the average (mean, etc.) of the differences determined in block 224. Other statistical measures of the change in representative pixel intensity for the subregions may additionally or alternatively be used to characterize the change in representative pixel intensity and arrive at a measure of the assessed relative motion between the image acquisition assembly and the object.

In some variations, assessing relative movement between the image acquisition assembly and the object being imaged may include subsampling the pixel intensities of the reflected light video frames. In particular, the relative movement may be assessed based on pixel intensities of a selected portion of the subregions (and accordingly, a selected number of the pixels). Such subsampling may reduce the overall computational complexity of the motion assessment. For example, as shown in FIG. 3, the relative movement may be based on a subsampling of subregions 342a that are distributed in an alternating checkerboard pattern. In this example, information from subregions 342a (shaded in FIG. 3) may be utilized in assessing relative motion, while information from subregions 342b (unshaded in FIG. 3) may be ignored. However, the motion assessment may incorporate any suitable sub sampling scheme (e.g., sampling different portions of the video frames, such as one-third, two-third, or another fraction of the subregions).

The method may additionally or alternatively include any other suitable motion-estimation algorithms using the pixel intensities and/or other characteristics of the reference video frames (e.g., based on a color component such as red, green, or blue of reference reflected light video frames, based on chroma values of reference reflected light video frames, etc.). In some variations, the method may additionally or alternatively include motion-estimation algorithms using the pixel intensities and/or other characteristics of the low light video frames (though, for example, using low light fluorescence video frames instead of reference reflected light video frames for motion-estimation may be less reliable in some circumstances). Additionally, in some variations in which the video frames include voxels, the method may include implementing the above-described motion-estimation algorithms with respect to characteristics of voxels (e.g., voxel intensity) instead of or in addition to characteristics of pixels (e.g., pixel intensity). Furthermore, in some variations the method may additionally or alternatively include receiving information from a gyroscope or other hardware configured to detect motion of the image acquisition assembly, and utilizing this information to assess movement of the image acquisition assembly.

The method may additionally or alternatively include any other suitable motion-estimation algorithms using the pixel intensities and/or other characteristics of the reflected light video frames (e.g., based on a color component such as red, green, or blue of reflected light video frames, based on chroma values of the reflected light video frames, etc.). In some variations, the method may additionally or alternatively include motion-estimation algorithms using the pixel intensities and/or other characteristics of the fluorescence frames (though, for example, using fluorescence video frames instead of the reflected light video frames for motion-estimation may be less reliable in some circumstances).

Between iterations, one or more of the values calculated during motion assessment may be stored in memory for future use. For example, the representative pixel intensities for the subregions in a current video frame may be stored for use in a future iteration of the calculations, to be used as the representative pixel intensities for the subregions in a previous video frame.

Adjusting the Level of Image Processing

Generally, the method may include selecting an imaging mode suitable for different amounts of relative movement between the image acquisition assembly and the object being imaged. In some variations, upon selection of an imaging mode, the method includes adjusting a level of image processing of the low light video frames 140 (e.g., fluorescence video frames) based on the relative movement (or assessment of relative movement) between the image acquisition assembly and the object being imaged. The level of image processing may be adjusted in order to increase sensitivity and/or reduce noise in the characteristic fluorescence video output.

For instance, upon selection of an imaging mode, adjusting the level of image processing of the low light video frames may include adjusting the quantity of low light video frames from which the characteristic low light video output is generated. At least some of the imaging modes may correspond to a respective, predetermined plural quantity of low light video frames that may be combined (as described in further detail below) to generate a characteristic low light video output with amplified or enhanced low light data from the combined low light video frames. However, more motion artifacts (e.g., motion blur) may appear in the characteristic low light video output if there is a significant amount of relative movement between the image acquisition assembly and the object throughout the combined low light video frames. Thus, in order to reduce motion artifacts in the characteristic low light video output, the quantity of low light video frames that is used to generate each frame of the characteristic low light video output may generally be inversely related to the degree of relative movement between the image acquisition assembly and the object being imaged.

For example, as shown in FIG. 4, a "low-motion mode" may correlate to a relatively high quantity of low light video frames (e.g., fluorescence video frames) that are combined to generate a frame of the low light video output during the low-motion mode. This low-motion mode may be suitable, for instance, when there are no or negligible changes in relative positions of the image acquisition assembly and the object being imaged. A "moderate-motion mode" may correlate to a moderate quantity of low light video frames that are combined to generate a frame of the low light video output during the moderate-motion mode. This moderate-motion mode may be suitable, for instance, when there are small or slight changes in relative positions of the image acquisition assembly and the object being imaged. A "high-motion mode" may correlate to a relatively low quantity (e.g., one) of low light video frames that are combined to generate a frame of the low light video output during the high-motion mode. This high-motion mode may be suitable, for instance, when there are major changes in relative positions of the image acquisition assembly and the object being imaged, and when it is desirable to avoid smearing or motion blur of the fluorescence image features and/or desirable to reduce the time lag in the displayed fluorescence video output.

Although FIG. 4 depicts an exemplary embodiment of the method with three imaging modes, other embodiments of the method may have fewer (e.g., 2) or more (e.g., 4, 5, or 6, etc.) imaging modes following a similar trend with respect to quantity of low light video frames (e.g., fluorescence video frames) that are combined to generate the characteristic low light video output (e.g., fluorescence video output).

Referring to FIG. 2A, after a measure representative of the assessed relative movement between the image acquisition assembly and the object is determined (226), the measure may be compared to one or more motion thresholds. Based on these comparisons, the particular imaging mode may be set to low-motion mode (252), moderate-motion mode (254), or high-motion mode (256). Subsequently, adjusting the level of image processing of the low light video frames (e.g., fluorescence video frames) may include adjusting the quantity of low light video frames from which the characteristic low light video output is generated, according to the set imaging mode.

More specifically, if the measure representative of the assessed relative movement is below a low-motion threshold (242), then the method may set the imaging system to a low-motion mode (252) such that adjusting the quantity of low light video frames involves setting the quantity of low light video frames (from which the characteristic low light video output is generated) to a predetermined high value. Additionally, if the measure is above the low-motion threshold (242), then the measure may be compared to a high-motion threshold (244). If the measure is above the low-motion threshold but below the high-motion threshold (244), then the method may set the imaging system to a moderate-motion mode (254) such that adjusting the quantity of low light video frames involves setting the quantity of low light video frames to a predetermined moderate value that is lower than the predetermined high value. If the measure is above the high-motion threshold (244), then the method may set the imaging system to a high-motion mode (256) such that adjusting the quantity of low light video frames involves setting the quantity of low light video frames (from which the characteristic low light video output is generated) to a predetermined low value that is lower than the predetermined moderate and high values.

In some variations, when the imaging system is set to a new imaging mode, the method may include gradually increasing or decreasing the quantity of low light video frames (from which the characteristic low light video output is generated) to the predetermined value associated with the new imaging mode. For instance, the gradual increasing or decreasing may occur over a series of frames of the characteristic low light video output, as defined by a predetermined number of frames or a predetermined period of time. This gradual change may help provide a smooth visual transition between previously-selected and currently-selected imaging modes. For example, when transitioning to the low-motion mode, setting the quantity of low light video frames to the predetermined high value may include gradually increasing the quantity of low light video frames. Similarly, when transitioning from the low-motion or the high-motion imaging mode to the moderate-motion mode, setting the quantity of low light video frames to the predetermined mid value may include gradually decreasing or increasing, respectively, the quantity of low light video frames. When transitioning to the high-motion mode, setting the quantity of low light video frames to the predetermined low value may include gradually decreasing the quantity of low light video frames in some variations. However, in some variations, it may be particularly desirable to immediately set the quantity to the predetermined low value when transitioning to the high-motion mode, to reduce motion artifacts in the low light video output when they are most likely to occur.

Generating a Characteristic Image

The method may include generating a characteristic low light video output 160 (e.g., a fluorescence video output) from the quantity of low light video frames (e.g., fluorescence video frames) based on the adjusted level of image processing. Generally, the quantity of low light video frames may be combined into a frame of the characteristic low light video output such that the low light video output visualizes amplified and/or de-noised low light image data from the combined low light video frames.

Figure 5:
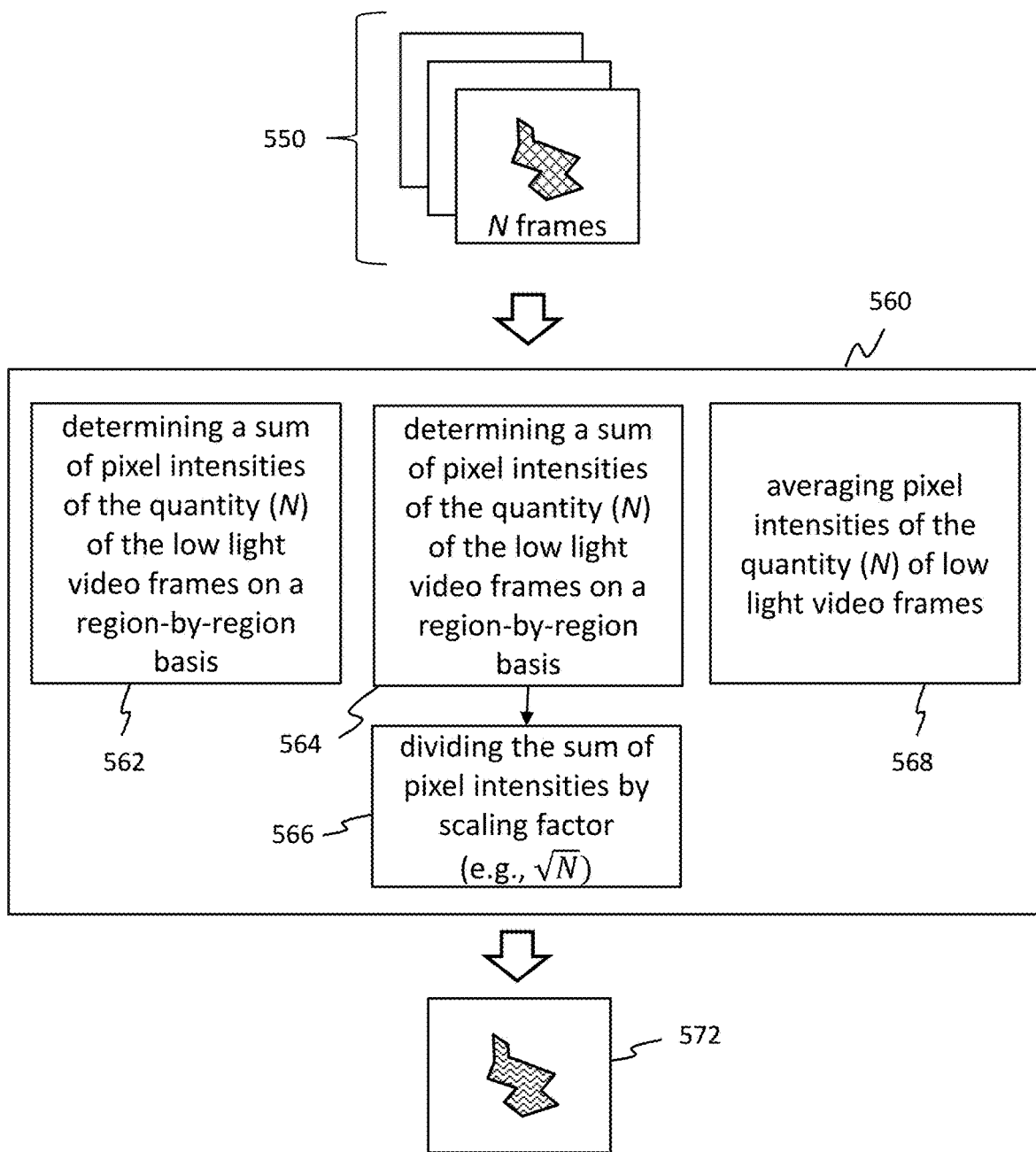
FIG. 5 is an illustrative schematic of variations of generating a characteristic low light video output.

As shown in FIG. 5, given a quantity N of low light video frames 550 (e.g., fluorescence video frames), the N frames may be combined in any one or more of several manners to generate a particular frame of the characteristic low light video output. In one variation, generating the characteristic low light video output 560 may include determining a sum of pixel intensities of the N low light video frames 550 on a region-by-region basis 562. Summing the pixel intensities may increase the low light signal intensity in the characteristic low light video output.

In another variation, generating the characteristic low light video output 560 (e.g., fluorescence video output) may include determining a sum of pixel intensities of the N low light video frames 550 on a region-by-region basis 564 (similar to 562) and further dividing the sum of the pixel intensities by a scaling factor 566, such as the square root of the number of video frames N. Other suitable scaling factors besides solely the square root of N may additionally or alternatively be used to scale the sum of the pixel intensities. This variation may partially increase the low light signal intensity in the characteristic low light video output, while limiting or eliminating any corresponding increase in the intensity of the image noise.

In yet another variation, generating the characteristic low light video output 560 may include averaging the pixel intensities of the quantity N of low light video frames 568. This may preserve the low light signal intensity in the characteristic low light video output, but may additionally reduce the intensity of image noise (that is, increase the signal-to-noise ratio).

In other variations, the characteristic low light video output may be generated from a selected quantity of low light video frames 550 in other suitable manners.

Other Low Light Imaging Adjustments

In another variation, at least some of the imaging modes may additionally or alternatively correspond to a respective low light video frame (e.g., a respective fluorescence video frame) exposure period. Longer exposure periods allow for an amplified low light image signal, but are also associated with a higher risk of motion artifacts resulting from relative movement between the image acquisition assembly and the object throughout the exposure period. Thus, in order to reduce motion artifacts in the characteristic low light video output, the duration of the exposure period may generally be inversely related to the degree of relative movement between the image acquisition assembly and the object being imaged. For example, as shown in FIG. 4, a low-motion mode imaging may be associated with a relatively high exposure (i.e., relatively longer period of time), a moderate-motion imaging mode may be associated with a moderate exposure, and a high-motion imaging mode may be associated with a relatively low exposure (i.e., relatively shorter period of time). Although FIG. 4 depicts an exemplary embodiment of the method with three imaging modes, other embodiments of the method may have fewer (e.g., 2) or more (e.g., 4, 5, or 6, etc.) imaging modes following a similar trend with respect to the low light video frame exposure period.

The adjustment of low light video frame exposure period may be supplemental to the multi-frame low light image processing described above for the different imaging modes. Alternatively, the adjustment of low light video frame exposure period may be performed without the multi-frame low light image processing, such that the method includes adjusting a low light video frame exposure period based at least in part on the relative movement between the image acquisition assembly and the object being imaged, and acquiring a sequence of low light video frames using the adjusted low light video frame exposure period.

Additionally, similar to the above-described gradual transition in the quantity of low light video frames being used for generating the characteristic low light video output, the transition between the imaging modes may involve gradually lengthening or shortening the low light video frame exposure period over a series of frames of the characteristic low light video output.

In other variations, such as for variations in which reference light video frames (e.g., reflected light video frames) and low light video frames (e.g., fluorescence video frames) are acquired with a single image sensor, the method may further include controlling a timing scheme of a visible light source that is illuminating the object, an excitation light source that is illuminating the object, and the image acquisition assembly. The timing scheme may be controlled based at least in part on the relative movement between the image acquisition assembly and the object. For instance, in one example, the timing scheme in a moderate-motion imaging mode may involve a repeated pattern of illumination and image processing for two successive reflective light video frames followed by one fluorescence light video frame. In a low-motion mode, the timing scheme may involve a repeated pattern of illumination and image processing for one reflective light video frame followed by two fluorescence light video frames which facilitates fluorescence image signal amplification and/or noise reduction in the characteristic fluorescence video output. Similar adjustments to the number of frames for fluorescence image acquisition may be performed for other variations of timing sequences.

Another example may be implemented in instances where two color component signals (e.g., green and blue) are continuously read on two of three channels on an image sensor while a third color component signal (e.g., red) and a fluorescence signal are alternatively read on the third channel of the image sensor. In this example, the timing scheme in a moderate-motion imaging mode may involve a repeated pattern of the illumination and image processing for two successive video frames with the third color component and one video frame with the fluorescence (e.g., GB+R, GB+R, GB+FL). In a low-motion imaging mode, the timing scheme may involve a repeated pattern of illumination and image processing for one video frame with the third color component and two successive video frames with the fluorescence (e.g., GB+R, GB+FL, GB+FL) which facilitates fluorescence image signal amplification and/or noise reduction in the characteristic fluorescence video output. Similar adjustments to the number of frames for fluorescence image acquisition may be performed for other variations of timing sequences.

In yet another variation, the method may include applying image stabilization technology to compensate for at least some ranges of motion or relative movement between the image acquisition assembly and the object (e.g., due to unsteady handling of the image acquisition assembly). The image stabilization technology may, for example, be implemented in hardware and/or image processing software, either as part of the imaging system or as a separate plug-in electronic image stabilization module. For instance, the level of image processing of the low light video frames (e.g., fluorescence video frames) may be adjusted based on an assessment of the residual evidence of relative movement that remains in at least a portion of the acquired sequence of reference video frames (e.g., reflected light video frames) after compensation by the image stabilization technology (e.g., instead of based on the actual, greater amount of relative movement determinable from video frames without compensation by the image stabilization technology).

Displaying

As shown in FIG. 1A, the method may include displaying at least one of the characteristic low light video output (e.g., fluorescence video output) and the reference video frames 170 (e.g., reflected light video frames) on a display (e.g., monitor or screen). In some instances (e.g., based on operator-selected settings), the method may include displaying both the characteristic low light video output and the sequence of reference video frames, either side-by-side or overlaid or otherwise merged. If the characteristic low light video output and the sequence of reference video frames are merged, then the low light video output may be displayed in high contrast to the reference video frames such as in a display color that is not commonly present in the body (e.g., bright green, purple). Similarly, the method may include displaying low light video frames acquired using an adjusted low light video frame exposure period, and/or the reference video frames either side-by-side or merged as described above.

The method may include storing or printing at least some frames of the characteristic low light video output, acquired low light video frames, and/or acquired reference video frames. For instance, desired video frames may be selected by the user via a user interface for storing in a memory unit, display, printing, etc.

Adaptive Imaging System

Figure 6A:
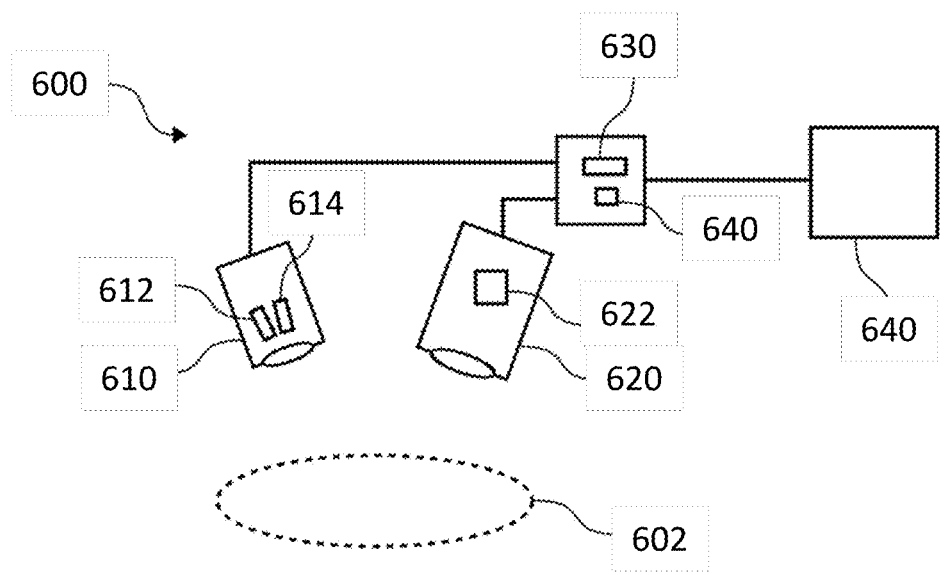
FIG. 6A is an illustrative schematic of one variation of an adaptive imaging system for generating low light video of an object according to an embodiment.

Generally, as shown in FIG. 6A, an example of an adaptive imaging system 600 for generating low light video of an object 602 (e.g., a tissue region of interest) may include: an image acquisition assembly 620 with at least one image sensor 622 configured to acquire a sequence of low light video frames depicting the object; and a processor 630. The processor 630 is configured to assess relative movement between the image acquisition assembly 620 based on reference video frames comprising at least a portion of the low light video frames and/or a portion of a substantially simultaneously acquired sequence of higher intensity video frames, adjust a level of processing of the low light video frames based at least in part on the relative movement between the image acquisition assembly 620 and the object 602, and generate a characteristic low light video output from a quantity of the low light video frames, wherein the quantity of the low light video frames is based on the adjusted level of image processing of the low light video frames. In other variations, the processor 630 may be configured to perform aspects of the method 100 described above.

Figure 6B:
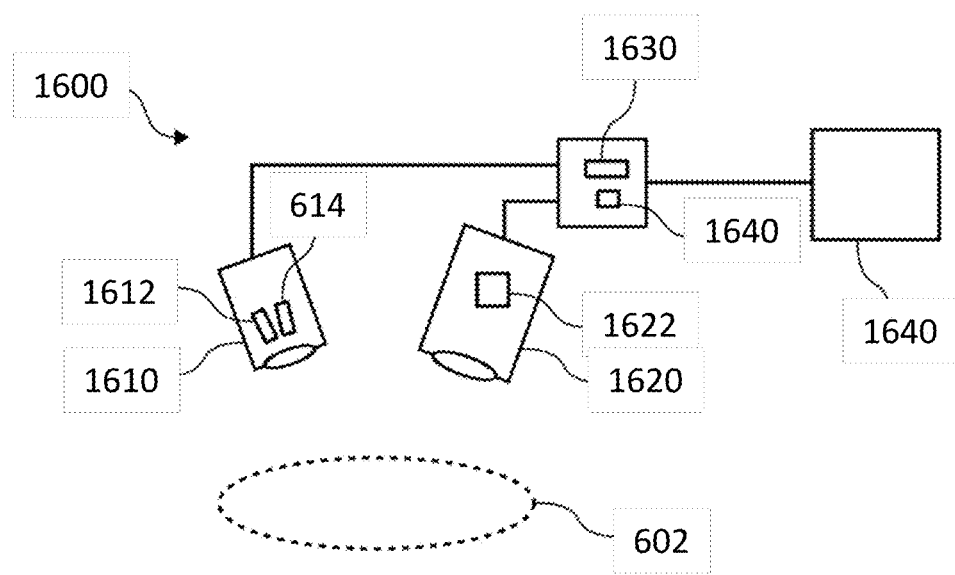
FIG. 6B is an illustrative schematic of one variation of an adaptive imaging system for generating fluorescence video of an object according to an embodiment.

In accordance with some embodiments, as shown in FIG. 6B, an example of an adaptive imaging system 1600 for generating fluorescence video of an object 1602 (e.g., a tissue region of interest) may include: an image acquisition assembly 1620 with at least one image sensor 1622 configured to acquire a sequence of reflected light video frames and a sequence of fluorescence video frames depicting the object; and a processor 1630. The processor 1630 is configured to assess relative movement between the image acquisition assembly 1620 based on at least a portion of the reflected light video frames, adjust a level of processing of the fluorescence video frames based at least in part on the relative movement between the image acquisition assembly 1620 and the object 1602, and generate a characteristic fluorescence video output from a quantity of the fluorescence video frames, wherein the quantity of the fluorescence video frames is based on the adjusted level of image processing of the fluorescence video frames. In other variations, the processor 1630 may be configured to perform aspects of the method 1100 described above.

Figure 7:
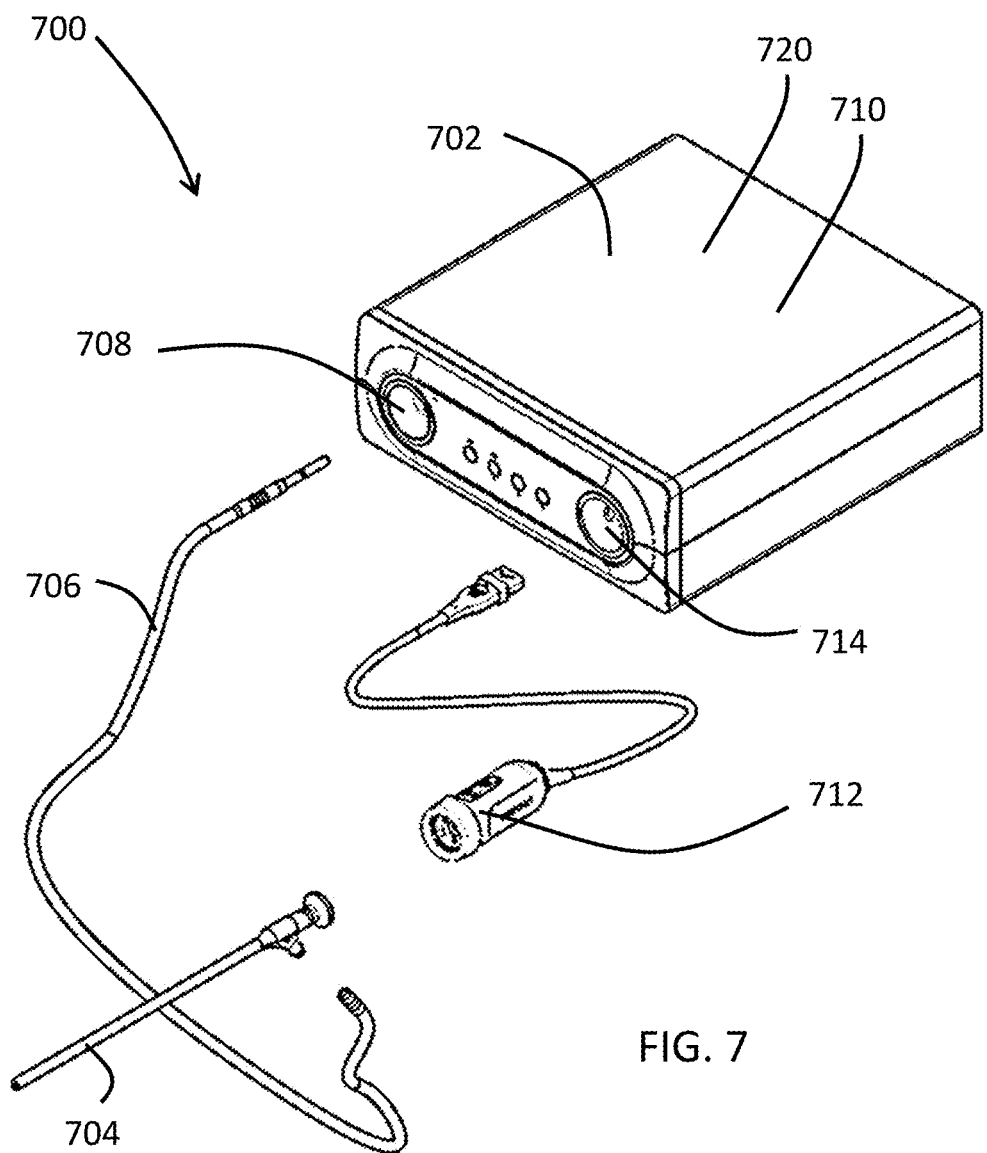
FIG. 7 is an illustrative depiction of one variation of an adaptive imaging system embodied in an endoscopic imaging system according to an embodiment.

In some variations, at least part of the adaptive imaging system may be embodied in an endoscopic imaging system, such as for minimally-invasive procedures. For example, as shown in FIG. 7, an endoscopic imaging system 700 may include an illuminator 702 with a light source assembly configured to provide visible light and/or fluorescence excitation light to a surgical laparoscope 704 via a light guide 706 that is connected to the illuminator 702 via a light guide port 708. A processor 710 and/or controller 720 may, in some variations, be within the same housing as the illuminator 702, as shown in FIG. 7, and may be configured to perform at least some of the aspects of the method 100 described above. An image acquisition assembly 712 may receive signals via connection to the laparoscope 704, and may pass acquired images to the processor 710 via connection to the processor 710 such as through port 714. Certain aspects of the light source assembly, image acquisition assembly, processor, and/or controller may be similar to those described in more detail below.

Light Source Assembly

As shown in the schematic of FIG. 6A, the imaging system 600 may include a light source assembly 610 including a visible light source 612 that emits visible light (e.g., full spectrum visible light, narrow band visible light, or other portions of the visible light spectrum) and/or an excitation light source 614 that emits excitation light for exciting fluorophores in the object 602 and causing fluorescence emission.

The visible light source 612 is configured to emit visible light for illumination of the object to be imaged. In some variations, the visible light source may include one or more solid state emitters, such as LEDs and/or laser diodes. For example, the visible light source may include blue, green, and red (or other color components) LEDs or laser diodes that in combination generate white light illumination. These color component light sources may be centered around the same wavelengths around which the image acquisition assembly (described further below) is centered. For example, in variations in which the image acquisition assembly includes a single chip, single color image sensor having an RGB color filter array deposited on its pixels, the red, green, and blue light sources may be centered around the same wavelengths around which the RGB color filter array is centered. As another example, in variations in which the image acquisition assembly includes a three-chip, three-sensor (RGB) color camera system, the red, green, and blue light sources may be centered around the same wavelengths around which the red, green, and blue image sensors are centered.

The excitation light source 614 is configured to emit excitation light suitable for exciting intrinsic fluorophores and/or extrinsic fluorophores (e.g., a fluorescence imaging agent introduced into the object) located in the object being imaged. The excitation light source 614 may include, for example, one or more LEDs, laser diodes, arc lamps, and/or illuminating technologies of sufficient intensity and appropriate wavelength to excite the fluorophores located in the object being imaged. For example, the excitation light source may be configured to emit light in the near-infrared (NIR) waveband (such as, for example, approximately 805 nm light), though other excitation light wavelengths may be appropriate depending on the application.

Figure 8:
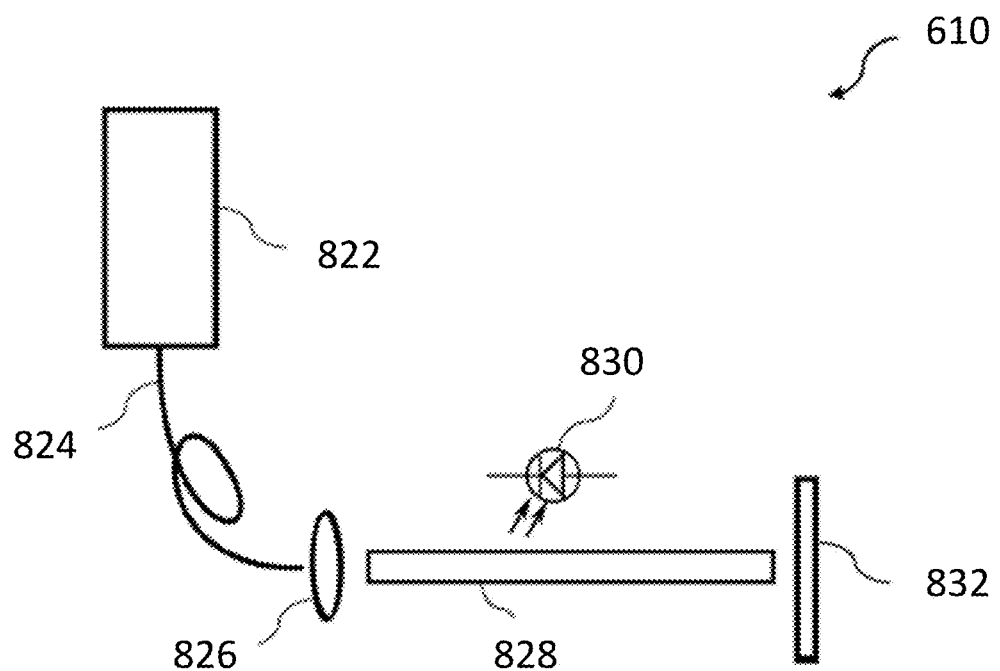
FIG. 8 is an illustrative schematic of one variation of a light source assembly in an adaptive imaging system according to an embodiment.

The light source assembly 610 may further include one or more optical elements that shape and/or guide the light output from the visible light source 612 and/or excitation light source 614. The optical components may include one or more lenses, mirrors (e.g., dichroic mirrors), light guides and/or diffractive elements, e.g., so as to help ensure a flat field over substantially the entire field of view of the image acquisition assembly 620. For example, as shown in the schematic of FIG. 8, the output 824 from a laser diode 822 (providing visible light or excitation light) may be passed through one or more focusing lenses 826, and then through a light guide 828. The light may be further passed through an optical diffractive element 832 (e.g., one or more optical diffusers). Power to the laser diode 822 may be provided by, for example, a high-current laser driver and may optionally be operated in a pulsed mode during the image acquisition process according to a timing scheme. An optical sensor such as a solid state photodiode 830 may be incorporated into the light source assembly and may sample the illumination intensity produced by one or more of the light sources, via scattered or diffuse reflections from the various optical elements.

Image Acquisition Assembly

Figure 9:
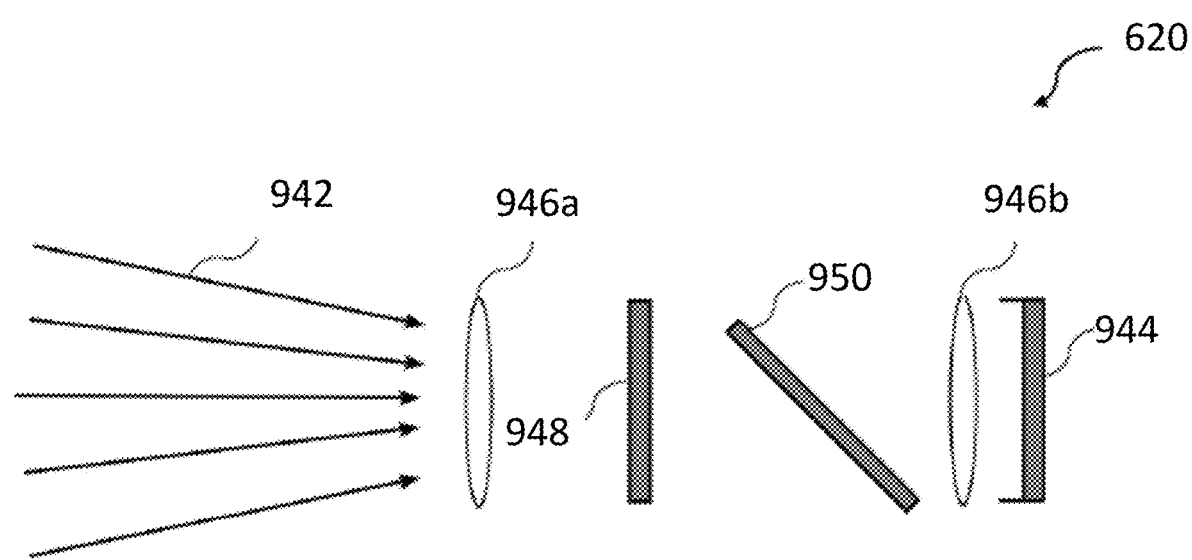
FIG. 9 is an illustrative schematic of one variation of an image acquisition assembly in an adaptive imaging system according to an embodiment.

The image acquisition assembly 620 may acquire reflected light video frames based on visible light that has reflected from the object, and/or fluorescence video frames based on fluorescence emitted by fluorophores in the object that are excited by the fluorescence excitation light. As shown in FIG. 9, the image acquisition assembly 620 may acquire images using a system of optics (e.g., one or more lenses 946*a*, one or more filters 948, one or more mirrors 950, beam splitters, etc.) to collect and focus reflected light and/or fluorescent light 942 onto an image sensor assembly 944. The image sensor assembly 944 may include at least one solid state image sensor. The one or more image sensors may include, for example, a charge coupled device (CCD), a CMOS sensor, a CID, or other suitable sensor technology. In one variation, the image sensor assembly 944 may include a single chip, single image sensor (e.g., a grayscale image sensor or a color image sensor having an RGB color filter array deposited on its pixels). In another variation, the image acquisition assembly may include a three-chip, three-sensor (RGB) image sensor assembly 944.

Processor and Controller

As shown in the schematic of FIG. 6A, the system may include a processor 630. The processor may include, for example, a microprocessor or other suitable central processing unit. In particular, the processor 630 may be configured to execute instructions to perform aspects of the methods described herein. As the low light video frames and/or the reference video frames are acquired, at least a portion of them may be stored in a memory unit for record-keeping purposes and/or retrieval for analysis during other aspects of the method, as described below.

As shown in the schematic of FIG. 6A, the system may include a controller 640, which may be embodied in, for example, a microprocessor and/or timing electronics. In some variations, a single image sensor may be used to acquire both low light video frames and reference video frames, and the controller 640 may control a timing scheme for the visible light source and/or the excitation light source, and the image acquisition assembly. This timing scheme may enable separation of the image signal associated with the low light signal and the image signal associated with the higher intensity reference light signal. In particular, the timing scheme may involve illuminating the object with illumination light and/or excitation light according to a pulsing scheme, and processing the low light image signal and reference image signal with a processing scheme, wherein the processing scheme is synchronized and matched to the pulsing scheme (e.g., via a controller) to enable separation of the two image signals in a time-division multiplexed manner. Examples of such pulsing and image processing schemes have been described in U.S. Pat. No. 9,173,554, filed on Mar. 18, 2009 and titled "IMAGING SYSTEM FOR COMBINED FULL-COLOR REFLECTANCE AND NEAR-INFRARED IMAGING," the contents of which are incorporated in their entirety by this reference. However, other suitable pulsing and image processing schemes may be used to acquire reference video frames and low light video frames simultaneously, for example to acquire reflected light video frames and fluorescence video frames simultaneously. Furthermore, the controller may be configured to control the timing scheme for the visible light source and/or the excitation light source, and the image acquisition assembly based at least in part on the relative movement between the image acquisition assembly and the object.

Other Hardware

In some variations, the system may include image stabilizing technology that helps compensate for some ranges of motion (e.g., caused by unsteady hands holding the image acquisition assembly) in the acquired low light images and/or reference images. The image stabilizing technology may be implemented in hardware, such as with optical image stabilization technology that counteracts some relative movement between the image acquisition assembly and the object by varying the optical path to the image sensor (e.g., lens-based adjustments and/or sensor-based adjustments). Additionally, or alternatively, the image stabilization technology may be implemented in software, such as with digital image stabilization that counteracts some relative movement between the image acquisition assembly and the object (e.g., by shifting the electronic image between video frames, utilizing stabilization filters with pixel tracking, etc.). Such image stabilizing technology may, for example, help correct for motion blur in the characteristic low light video output (or in the acquired low light video frames) resulting from relative motion during long exposure periods or the combination of multiple low light video frames.

The system may, in some variations, include one or more hardware motion sensors (e.g., gyroscope, accelerometer) that measure absolute motion of the image acquisition assembly. Information from these motion-measuring sensors may be used, in addition or as an alternative to the above-described motion-estimation algorithms, to determine which imaging mode of the system is suitable for a given set of circumstances.

Additionally, the system may include one or more data modules 640 that communicates and/or stores some or all of the acquired reference video frames, acquired low light video frames, characteristic low light video output, and/or information generated from the image data. For instance, the data module 640 may include a display (e.g., computer screen or other monitor), recorder or other data storage device, printer, and/or picture archiving and communication system (PACS). The system may additionally or alternatively include any suitable systems for communicating and/or storing images and image-related data.

A kit may include any part of the systems described herein, and/or the tangible non-transitory computer-readable medium described above having computer-executable (readable) program code embedded thereon that may provide instructions for causing one or more processors, when executing the instructions, to perform one or more of the methods described herein. For instance, the instructions may cause one or more processors, when executing the instructions, to perform an adaptive imaging method for generating low light video of an object. The method comprises receiving a sequence of low light video frames depicting the object, wherein the low light video frames are acquired by an image acquisition assembly; assessing relative movement between the image acquisition assembly and the object based on reference video frames comprising at least a portion of the low light video frames and/or a portion of a substantially simultaneously acquired sequence of higher light intensity video frames; adjusting a level of image processing of the low light video frames based at least in part on the relative movement between the image acquisition assembly and the object; and generating a characteristic low light video output from a quantity of low light video frames, wherein the quantity of the low light video frames is based on the adjusted level of image processing of the low light video frames. Furthermore, the kit may include instructions for use of at least some of its components (e.g., for installing the computer-executable (readable) program code with instructions embedded thereon, etc.).

In other variations, a kit may include any part of the systems described herein and a fluorescence agent such as, for example, a fluorescence dye such as ICG or any suitable fluorescence agent or a combination of fluorescence agents. In some variations, a suitable fluorescence agent is an agent which can circulate with the blood (e.g., an agent which can circulate with, for example, a component of the blood such as plasma in the blood) and which fluoresces when exposed to appropriate excitation light energy. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement. According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 μM to about 10 μM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 μM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. An example of the fluorescence agent is a fluorescence dye, which includes any non-toxic fluorescence dye. In certain variations, the fluorescence dye may include a dye that emits light in the near-infrared spectrum. In certain embodiments, the fluorescence dye may include a tricarbocyanine dye such as, for example, indocyanine green (ICG). In other variations, the fluorescence dye may comprise methylene blue, ICG or a combination thereof. In certain embodiments the dye is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the medical imaging modality.

In some variations, the fluorescence imaging agent used in combination with the methods, systems and kits described herein may be used for blood flow imaging, tissue perfusion imaging, lymphatic imaging, or a combination thereof, which may be performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations, such lymphatic imaging may relate to the female reproductive system (e.g., uterus, cervix, vulva).

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICGadministration. Using a TB syringe and a 30G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to high-light/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

One or more embodiments are directed to a fluorescence imaging agent for use in the imaging systems and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. An adaptive imaging method for generating enhanced low-intensity light video of an object for medical visualization, comprising:
   acquiring, with an image acquisition assembly, a sequence of low light video frames depicting the object;
   receiving a sequence of reference video frames;
   assessing relative movement between the image acquisition assembly and the object based on the reference video frames;
   adjusting a level of image processing of the low light video frames based at least in part on the relative movement between the image acquisition assembly and the object; and
   generating a characteristic low light video output from a quantity of the low light video frames, wherein the quantity of the low light video frames is based on the adjusted level of image processing of the low light video frames, wherein generating the characteristic low light video output comprises determining a sum of pixel intensities of the quantity of the low light video frames on a region-by-region basis, wherein generating the characteristic low light video output further comprises dividing the sum of pixel intensities by the square root of the quantity of the low light video frames.

2. The method of claim 1, wherein the sequence of reference video frames comprises frames from the sequence of low light video frames.

3. The method of claim 1, further comprising acquiring, with the image acquisition assembly, a sequence of higher intensity light video frames generally having a higher light intensity than the low light video frames, wherein the sequence of higher intensity light video frames are acquired substantially simultaneously with the sequence of low light video frames.

4. The method of claim 3, wherein the sequence of reference video frames comprises frames from the sequence of higher intensity light video frames.

5. The method of claim 1, wherein assessing relative movement between the image acquisition assembly and the object comprises measuring changes in pixel intensities in a plurality of the reference video frames.

6. The method of claim 1, wherein assessing relative movement between the image acquisition assembly and the object comprises determining a representative pixel intensity for each of a plurality of subregions in the plurality of reference video frames, and characterizing the changes in representative pixel intensity for the subregions in the plurality of the reference video frames.

7. The method of claim 1, wherein adjusting the level of image processing of the low light video frames comprises adjusting the quantity of low light video frames from which the characteristic low light video output is generated.

8. The method of claim 1, wherein adjusting the quantity of low light video frames comprises setting the quantity of low light video frames to a first predetermined value if the relative movement between the image acquisition assembly and the object is below a first motion threshold.

9. The method of claim 8, wherein setting the quantity of low light video frames to the first predetermined value comprises gradually increasing or decreasing the quantity of low light video frames to the first predetermined value over a series of frames of the characteristic low light video output.

10. The method of claim 9, wherein adjusting the quantity of low light video frames comprises setting the quantity of low light video frames to a second predetermined value if the relative movement between the image acquisition assembly and the object is above the first motion threshold, the second predetermined value being lower than the first predetermined value.

11. The method of claim 10, wherein setting the quantity of low light video frames to the second predetermined value comprises gradually increasing or decreasing the quantity of low light video frames to the second predetermined value over a series of frames of the characteristic low light video output.

12. The method of claim 11, wherein adjusting the quantity of low light video frames comprises:

setting the quantity of low light video frames to the second predetermined value if the relative movement between the image acquisition assembly and the object is above the first motion threshold and below a second motion threshold higher than the first motion threshold; and setting the quantity of low light video frames to a third predetermined value, if the relative movement between the image acquisition assembly and the object is above the first and second motion thresholds, the third predetermined value being lower than the first and second predetermined values.

13. The method of claim 12, wherein setting the quantity of low light video frames to the third predetermined value comprises gradually increasing or decreasing the quantity of low light video frames to the third predetermined value over a series of frames of the characteristic low light video output.

14. The method of claim 13, wherein adjusting the quantity of low light video frames comprises gradually increasing or decreasing the quantity of low light video frames toward a predetermined value over a series of frames of the characteristic low light video output.

15. The method of claim 1, wherein generating the characteristic low light video output from the quantity of the low light video frames comprises averaging pixel intensities of the quantity of the low light video frames on a region-by-region basis.

16. The method of claim 15, further comprising adjusting a low light video frame exposure period based at least in part on the relative movement between the image acquisition assembly and the object.

17. The method of claim 1, further comprising displaying at least one of the characteristic low light video output and the reference video frames on a display.

18. The method of claim 1, further comprising controlling a timing scheme of a visible light source illuminating the object, an excitation light source illuminating the object, and the image acquisition assembly based at least in part on the relative movement between the image acquisition assembly and the object.

19. The method of claim 1, wherein the method is performed continuously.

20. The method of claim 1, wherein the sequence of low light video frames comprises a sequence of fluorescence video frames.

21. The method of claim 1, wherein the sequence of low light video frames comprises a sequence of reflected light video frames.

22. The method of claim 1, wherein the sequence of reference video frames comprises a sequence of reflected light video frames.

23. An adaptive imaging system for generating enhanced low-intensity light video of an object for medical visualization, comprising:

an image acquisition assembly configured to acquire a sequence of low light video frames depicting the object;

one or more processors;

memory; and one or more programs, wherein the one or more programs are stored in the memory and configured to be executed by the one or more processors, the one or more programs including instructions for:

assessing relative movement between the image acquisition assembly and the object based on reference video frames;

adjusting a level of image processing of the low light video frames based at least in part on the relative movement between the image acquisition assembly and the object; and generating a characteristic low light video output from a quantity of the low light video frames, wherein the quantity of the low light video frames is based on the adjusted level of image processing of the low light video frames, wherein generating the characteristic low light video output comprises determining a sum of pixel intensities of the quantity of the low light video frames on a region-by-region basis, wherein generating the characteristic low light video output further comprises dividing the sum of pixel intensities by the square root of the quantity of the low light video frames.

24. A fluorescence imaging agent for use with the method of claim 1 for imaging an object during blood flow imaging, tissue perfusion imaging, lymphatic imaging, or a combination thereof.

* * * * *